(12) United States Patent
Ogawa et al.

(10) Patent No.: US 10,358,666 B2
(45) Date of Patent: Jul. 23, 2019

(54) ALGAE AND METHOD FOR PRODUCING SAME, AND METHOD FOR PRODUCING BIOMASS USING SAID ALGAE

(71) Applicant: JAPAN SCIENCE AND TECHNOLOGY AGENCY, Kawaguchi-shi, Saitama (JP)

(72) Inventors: Ken'ichi Ogawa, Okayama (JP); Masanobu Nishikawa, Okayama (JP); Kazuya Kiyokawa, Okayama (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 0 days.

(21) Appl. No.: 15/314,868

(22) PCT Filed: May 26, 2015

(86) PCT No.: PCT/JP2015/002634
§ 371 (c)(1),
(2) Date: Nov. 29, 2016

(87) PCT Pub. No.: WO2015/182110
PCT Pub. Date: Dec. 3, 2015

(65) Prior Publication Data
US 2017/0218415 A1 Aug. 3, 2017

(30) Foreign Application Priority Data

May 29, 2014 (JP) .................... 2014-111577

(51) Int. Cl.
| | | |
|---|---|---|
| *C12P 5/00* | (2006.01) | |
| *C12P 19/04* | (2006.01) | |
| *C12N 15/09* | (2006.01) | |
| *C12N 15/113* | (2010.01) | |
| *C12P 1/00* | (2006.01) | |
| *C12P 7/64* | (2006.01) | |
| *C08B 30/00* | (2006.01) | |
| *C12N 1/12* | (2006.01) | |
| *C12N 15/79* | (2006.01) | |

(52) U.S. Cl.
CPC ............. *C12P 19/04* (2013.01); *C08B 30/00* (2013.01); *C12N 1/12* (2013.01); *C12N 15/09* (2013.01); *C12N 15/113* (2013.01); *C12N 15/79* (2013.01); *C12P 1/00* (2013.01); *C12P 7/64* (2013.01)

(58) Field of Classification Search
None
See application file for complete search history.

(56) References Cited

U.S. PATENT DOCUMENTS

| | | |
|---|---|---|
| 2013/0143260 A1 | 6/2013 | Ogawa et al. |
| 2015/0159178 A1 | 6/2015 | Green et al. |

FOREIGN PATENT DOCUMENTS

| | | |
|---|---|---|
| CN | 103068966 A | 4/2013 |
| CN | 103725717 A | 4/2014 |
| JP | H11196885 A | 7/1999 |
| JP | 2003310288 A | 11/2003 |
| JP | 2010088334 A | 4/2010 |
| WO | 2009153439 A2 | 12/2009 |
| WO | 2012029727 A1 | 3/2012 |

OTHER PUBLICATIONS

Molnar et al. (BMC Genomics, 2012, vol. 13, No. 576, pp. 1-28).*
International Search Report issued in PCT/JP2015/002634 dated Aug. 18, 2015—incl Engl lang transl.
Hyams and Davies, The Induction and Characterisation of Cell Wall Mutants of Chlamydomonas Reinhardi. Mutation Res., 1972;14(4):381-389.
Kiyokawa et al., Denpun Chikuseki ga Ko shin suru Hikari Kyodoji ni Okeru Chlamydomonas GSHI Kajo Hatsugen Kabu no Tanpakushitsu Bunkai Yokusei. [Suppression of proteolysis of strains overexpressing chlamydomonas GSH1 at light intensities in which starch accumulation is enhanced]. Summary of the 54th annual meeting of the Japanese Society of Plant Physiologists, Mar. 14, 2013, p. 307, PL026(0762)—incl Engl lang transl.
Li et al., Chlamydomonas starchless mutant defective in ADP-glucose pyrophosphorylase hyper-accumulates triacylglycerol. Metab Eng. Jul. 2010;12(4):387-391.
Merchant et al., The Chlamydomonas genome reveals the evolution of key animal and plant functions. Science. Oct. 12, 2007;318(5848):245-251.
Msanne, Abiotic Stress Responses in Photosynthetic Organisms. Dissertation: University of Nebraska, Dec. 2011: pp. 1-59 (part 1 due to size).
Msanne, Abiotic Stress Responses in Photosynthetic Organisms. Dissertation: University of Nebraska, Dec. 2011: pages 60-129 (part 2 due to size).
Tenenboim et al., VMPI-deficient Chlamydomonas exhibits severely aberrant cell morphology and disrupted cytokinesis. BMC Plant Biol. May 6, 2014;14:121.
Wang et al., Algal Lipid Bodies: Stress Induction, Purification, and Biochemical Characterization in Wild-Type and Starchless Chlamydomonas reinhardtii. Eukaryot Cell. Dec. 2009; 8(12):1856-1868.
The Extended European Search Report and Written Opinion issued in EP 15798847 dated Dec. 19, 2017 (6 pages).
Morell et al., Chap 10: Control of starch biosynthesis in vascular plants and algae. In Annual Plant Reviews, Control of Primary Metabolism in Plants, Edited by William C. Plaxton, Michael T. McManus Copyright © 2006 by Blackwell Publishing Ltd (pp. 258-289) Retrieved from the Internet:URL:http://epo.summon.serialssolutions.com/2.0.0/link/O/eLvHCXMwY2BQSUu2NEpONDXStUxNMdU1SbUwBbJME3XNUpMtk5MS08yTwde3RTqbhLibB7mb-.
Office Action issued by TIPO in Tawanese Patent Application No. 104117313 dated Mar. 28, 2019 (8 pages).

* cited by examiner

*Primary Examiner* — Hope A Robinson
(74) *Attorney, Agent, or Firm* — Acuity Law Group, PC; Michael A. Whittaker

(57) ABSTRACT

The present invention provides a method of biomass production using a modified alga having suppressed expression of ATG8.

4 Claims, 7 Drawing Sheets

Specification includes a Sequence Listing.

(a)

(b)

(a)

(b)

ALGAE AND METHOD FOR PRODUCING SAME, AND METHOD FOR PRODUCING BIOMASS USING SAID ALGAE

CROSS-REFERENCE TO RELATED APPLICATIONS

The present invention is filed under 35 U.S.C. § 371 as the U.S. national phase of International Patent Application No. PCT/JP2015/002634, filed 26 May 2015, which designated the U.S. and claims the benefit of priority to Japanese Patent Application No. 2014-111577, filed 29 May 2014, each of which is hereby incorporated in its entirety including all tables, figures and claims.

TECHNICAL FIELD

The present invention relates to a modified alga, a method of producing the same, and a method of biomass production using the modified alga. More specifically, the invention relates to a modified alga with increased photosynthetic productivity.

BACKGROUND ART

Fuels from biomass, or so-called biofuels (such as bioethanol and biodiesel, for example) are promising alternatives to fossil fuels.

Biomass, a raw material for biofuel, includes saccharides (for example, starch) and oils and fats, and is produced by plants through photosynthesis. Accordingly, plants which are capable of active photosynthesis and intracellular accumulation of saccharides or oils and fats can be used as biomass sources. Corn and soybean are major plants that are currently used for biomass production. These crops are also consumed as food and forage, and dramatic increases in biofuel production would lead to soaring prices of food and forage, which has been disputed.

Under such circumstances, algae are attracting attention as alternative biomass sources to corn and soybean (see, for example, PTLs 1 and 2). Algal biomass production has advantages such as compatibility with food and forage supply and the massive algal growth.

For example, some mutants of *Chlamydomonas*, an alga, are known which lack a cell wall or have a thinner cell wall (cw15 and cw92, for example). These mutants have properties convenient for introduction of exogenous DNA into cells, and have been broadly used in gene transfer experiments. They are also helpful for increasing biomass productivity in that their cell is easily disrupted and facilitates recovery of contents thereof, and thus are reported to be used for biomass production. For example, PTL 3 discloses production of oils and fats using a cell-wall-deficient *Chlamydomonas* mutant. NPL 1 reports that a *Chlamydomonas* mutant with the cell wall mutation (cw15) and deficiency of a starch synthesis gene releases lipid droplets outside the cell. NPL 2 reports that a cell wall mutant of *Chlamydomonas* (cw15) further knocked out for a starch synthesis gene has increased productivity of oils and fats. NPL 3 is a known report on cell wall mutants of *Chlamydomonas*.

PTL 4 reports a technique involving recovery of starch produced and extracellularly released by an algal source, *Chlorella*, and subsequent fermentation of the starch to produce ethanol. PTL 5 discloses a technique of modifying an alga to have an increased chloroplastic glutathione concentration for increasing its starch productivity.

CITATION LIST

Patent Literature

[PTL 1] Japanese Unexamined Patent Application Publication No. 11-196885
[PTL 2] Japanese Unexamined Patent Application Publication No. 2003-310288
[PTL 3] WO 2009/153439
[PTL 4] Japanese Unexamined Patent Application Publication No. 2010-88334
[PTL 5] WO 2012/029727

Non Patent Literature

[NPL 1] Zi Teng Wang, Nico Ullrich, Sunjoo Joo, Sabine Waffenschmidt, and Ursula Goodenough (2009) Eukaryotic Cell Vol. (12): 1856-1868. Algal Lipid Bodies: Stress Induction, Purification, and Biochemical Characterization in Wild-Type and Starchless *Chlamydomonas reinhardtii*.
[NPL 2] Yantao Li, Danxiang Han, Guongrong Hu, David Dauvillee, Milton Sommerfeld, Steven Ball and Qiang Hu (2010) Metabolic Engineering Vol. 12 (4): 387-391. *Chlamydomonas* starchless mutant defective in ADP-glucose pyrophosphorylase hyper-accumulates triacylglycerol.
[NPL 3] Jerry Hyams, D. Roy Davies (1972) Mutation Research 14 (4): 381-389. The induction and characterisation of cell wall mutants of *Chlamydomonas reinhardtii*.

SUMMARY OF INVENTION

Technical Problem

Unfortunately, the techniques of algal biomass production disclosed in PTLs 1 to 4 and NPLs 1 to 3 still need improvements in productivity. For example, biomass production involving culture of an alga under heterotrophic conditions where acetic acid serves as a carbon source requires a step of nutrient restriction, such as a step of providing a nitrogen-deficient condition, for inducing biomass production and accumulation in the alga. Algae are generally grown in a nitrogen-containing culture medium, and providing the nitrogen-deficient condition requires replacement of the culture medium with a nitrogen-free culture medium. It complicates the process, resulting in reduced productivity and increased costs. PTL 5 provides a solution to the issue, but the solution still has room for improvement in productivity.

The present invention was conceived as a solution to the existing issues, that is, an object of the invention is to provide a novel modified alga that can achieve increased biomass productivity, and use of the alga.

Solution to Problem

The inventors have made various studies mainly for the purpose of solving the issues, and have consequently found that suppression of ATG8 expression in algae can increase biomass productivity in algal cells. The invention was completed based on such finding.

The present invention involves the following aspects:
[1]. A modified alga having suppressed expression of ATG8 as compared to that of the reference strain.
[2]. The modified alga according to [1], wherein the alga overexpresses MEX1.

[3]. The modified alga according to [2], wherein the alga comprises an exogenous polynucleotide introduced therein, the exogenous polynucleotide encoding MEX1.

[4]. The modified alga according to [3], wherein the exogenous polynucleotide is one or more polynucleotides selected from the group consisting of:
(a) a polynucleotide encoding a polypeptide which comprises an amino acid sequence set forth in SEQ ID NO: 1 or SEQ ID NO: 3;
(b) a polynucleotide encoding a polypeptide which comprises an amino acid sequence derived from the amino acid sequence set forth in SEQ ID NO: 1 or SEQ ID NO: 3 and maintaining the function of MEX1 wherein one or more amino acids are deleted, substituted, or added in the amino acid sequence; and
(c) a polynucleotide which is hybridizable with a polynucleotide comprising a base sequence complementary to that of the polynucleotide (a) or (b) under stringent conditions and encodes a polypeptide having the function of MEX1.

[5]. The modified alga according to [1], wherein the alga includes an ATG8 gene silenced.

[6]. The modified alga according to [5], wherein the alga includes a miRNA introduced therein, the miRNA having a base sequence set forth in SEQ ID NO: 5.

[7]. The modified alga according to any one of [1] to [6], wherein the alga has an increased chloroplastic glutathione concentration as compared to that of the reference strain.

[8]. A method of producing a modified alga, the method involving an ATG8 expression suppressing step to suppress expression of ATG8.

[9]. The method according to [8], wherein the method involves a glutathione enrichment step to increase a chloroplastic glutathione concentration.

[10]. A method of biomass production using a modified alga that has a suppressed expression of ATG8 as compared to that of the reference strain.

[11]. The method according to [10], wherein the method involves a photoirradiation step to irradiate the alga with light.

[12]. The method according to [10] or [11], wherein the alga has an increased chloroplastic glutathione concentration as compared to that of the reference strain.

[13]. The method according to [12], wherein the photoirradiation step is carried out under conditions substantially without nitrogen deficiency.

[14]. The method according to [13], wherein the method involves no cell lysis step to disrupt algal cells.

[15]. Starch produced using a modified alga that has suppressed expression of ATG8 as compared to that of the reference strain.

[16]. The starch according to [15], wherein the alga has an increased chloroplastic glutathione concentration as compared to that of the reference strain.

As used herein, the term "reference strain" refers to an algal strain before an inventive modification. Specifically, "reference strain" refers to an algal strain before a treatment for suppression of ATG8 expression, more specifically to that before overexpression of MEX1 or silencing of ATG8. If a wild-type algal strain is subjected to an inventive modification, the term "reference strain" refers to the wild-type strain or an algal strain of the same species. If an algal strain produced by a preliminary modification (for example, modification to increase the chloroplastic glutathione concentration) is further subjected to an inventive modification, the term "reference strain" refers to the algal strain produced by the preliminary modification or an algal strain of the same species.

Advantageous Effects of Invention

The inventive alga has suppressed expression of ATG8, and thus can achieve increased intracellular photosynthetic productivity. Accordingly, the inventive method of biomass production provides algal biomass production with lower costs and higher efficiency than traditional methods.

DESCRIPTION OF EMBODIMENTS

Figure 1:
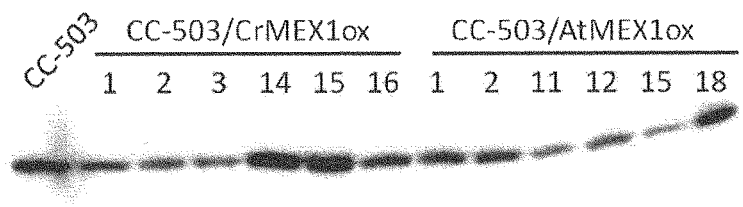
FIG. 1 illustrates the results of measurement of the ATG8 protein expressions in some of the "modified strains with suppressed expression of ATG8" produced in Example 1.

Embodiments of the present invention will now be described in details, but should not be construed to limit the invention. The invention can be practiced in embodiments with various modifications to the embodiments below within the scope of the disclosure. All of the academic and patent documents mentioned herein are incorporated by reference in its entirety. As used herein, the expression "A to B" indicating a numerical range indicates "from A to B, inclusive of A and B", unless otherwise specified.

1. Inventive Alga

The inventive alga may have any structure having suppressed intracellular expression of ATG8, and should preferably be an alga with increased photosynthetic productivity.

"ATG8" is an abbreviation for "autophagy-related protein 8" and is also referred to as APG8. ATG8 is a ubiquitin-like protein, and is known to form a conjugate with phosphatidylethanolamine (hereinafter, the conjugate is referred to as "ATG8-PE") and to be involved in the formation of autophagosomal membranes (see Nakatogawa H et al .

(2007) Cell 130: 165-178 (non-patent literature)). As used herein, "suppressed expression of ATG8" refers to reduced intracellular expression of ATG8 as compared to that of a reference strain. The reduction of intracellular expression of ATG8 is preferably determined if the intracellular ATG8 expression in an alga is 0.9 times or less, more preferably with at least 5% significant difference as determined by t-test, as compared to that of a reference strain cultured under the same conditions. The expression of ATG8 by the alga of the invention is, for example, 90% or less, 80% or less, 70% or less, 60% or less, 50% or less, 40% or less, 30% or less, 20% or less, 10% or less, or 0% (less than the lower limit of detection), of that of a reference strain (see Examples 2 and 4).

Intracellular expression of ATG8 in a reference strain is preferably measured at the same time and by the same method as an inventive alga, but may be determined based on accumulated background data. Intracellular expression of ATG8 in an alga can be determined by any conventional technique such as Western blotting.

As used herein, "increased photosynthetic productivity" refers to an increased production of photosynthate as compared to that of a reference strain. The increase in photosynthetic productivity is preferably determined if the production of photosynthate in an alga is 1.1 times or more, more preferably with at least 5% significant difference determined by t-test, as compared to that of a reference strain cultured under the same conditions. The productivity can be evaluated from various viewpoints including conditions of photoirradiation (for example, quantity of light, intensity and duration of irradiation), nutrients applied, productivity per unit time, whether or not a step of providing a nutrient-deficient condition is essentially required, and culture temperature.

As used herein, the term "photosynthate" refers to substances produced by algae through photosynthetic carbon fixation, specifically to biomass such as saccharides (for example, starch) and oils and fats and derivatives (such as metabolites) thereof. As used herein, "photosynthetic carbon fixation" is a general term for metabolism of carbon compounds using chemical energy derived from light energy. Accordingly, the origin of carbon to be incorporated in a metabolic pathway includes not only inorganic compounds such as carbon dioxide but also organic compounds such as acetic acid.

As used herein, the "alga" may be any alga that is capable of photosynthesis, that is, biosynthesis of photosynthate. Such an alga include, for example, microalgae belonging to the class Chlorophyceae within the phylum Chlorophyta. More specifically, examples of the alga include: species belonging to the genus *Chlamydomonas* within the class Chlorophyceae, such as *Chlamydomonas reinhardtii, Chlamydomonas moewusii, Chlamydomonas eugametos,* and *Chlamydomonas segnis;* species belonging to the genus *Scenedesmus* within the class Chlorophyceae, such as *Scenedesmus acumunatus, Scenedesmus dimorphus, Scenedesmus disciformis,* and *Scenedesmus ovaltermus;* species belonging to the genus *Dunaliella* within the class Chlorophyceae, such as *Dunaliella salina, Dunaliella tertiolecta,* and *Dunaliella primolecta;* species belonging to the genus *Chlorella* within the class Chlorophyceae, such as *Chlorella vulgaris* and *Chlorella pyrenoidosa;* species belonging to the genus *Haematococcus* within the class Chlorophyceae, such as *Haematococcus pluvialis;* species belonging to the genus *Chlorococcum* within the class Chlorophyceae, such as *Chlorococcum littorale;* species belonging to the genus *Botryococcus* within the class Chlorophyceae or *Xanthophyceae,* such as *Botryococcus braunii;* species belonging to the genus *Choricystis* within the class Chlorophyceae, such as *Choricystis minor;* species belonging to the genus *Pseudochoricystis* within the class Chlorophyceae, such as *Pseudochoricystis ellipsoidea;* species belonging to the genus *Amphora* within the class Diatomophyceae (e.g., *Amphora* sp.); species belonging to the genus *Nitzschia* within the class Diatomophyceae, such as *Nitzschia alba, Nitzschia closterium,* and *Nitzschia laevis;* species belonging to the genus *Crypthecodinium* within the class Dinophyceae, such as *Crypthecodiniumcohnii;* species belonging to the genus *Euglena* within the class Euglenophyceae, such as *Euglena gracilis* and *Euglena proxima;* species belonging to the genus *Paramecium* within the phylum Ciliophora, such as *Paramecium bursaria;* species belonging to the genus *Synechococcus* within the phylum Cyanobacteria, such as *Synechococcus aquatilis* and *Synechococcus elongatus;* species belonging to the genus *Spirulina* within the phylum Cyanobacteria, such as *Spirulina platensis* and *Spirulina subsalsa;* species belonging to the genus *Prochlorococcus* within the phylum Cyanobacteria, such as *Prochlorococcus marinus;* and species belonging to the genus *Oocystis* within the phylum Cyanobacteria, such as *Oocystis polymorpha.*

An alga with suppressed intracellular expression of ATG8 may be produced by any method that will be described in detail in a section explaining an inventive method of producing a modified alga.

In one embodiment, the inventive alga preferably has increased intracellular expression and/or activity of MEX1 (maltose transporter gene) as compared to that of a reference strain. MEX1 is known to serve in a cell as a transporter to deliver maltose from chloroplast to cytoplasm (see Niittyla T et al. (2004), Science 303 (5654): 87-89 (non-patent literature)). Overexpression of MEX1 in algae results in decreased expression of ATG8.

The inventive alga may include a polynucleotide that has been expressibly introduced therein and encodes an MEX1 protein. Introduction of such an exogenous polynucleotide suppresses intracellular expression of ATG8 in the alga through overexpression of MEX1.

In other words, the invention provides a transformed (modified) alga which includes a polynucleotide introduced therein and encoding an MEX1 protein and has suppressed intracellular expression of ATG8. Such a transformed alga achieves increased photosynthetic productivity as compared to a reference strain, as will be described below.

The MEX1 protein to be expressed in the alga or the polynucleotide encoding the MEX1 protein maybe from any origin if it can be introduced or expressed to exert its action in a host alga. Examples of such an MEX1 protein or a polynucleotide encoding the MEX1 protein include MEX1 proteins from the host alga, algae of other species than the host alga, and other plants, and polynucleotides encoding the MEX1 proteins. An MEX1 protein from other plant or a polynucleotide encoding the MEX1 protein is preferably derived from a plant belonging to the genus *Arabidopsis* within the class Dicotyledoneae, for example.

Specific examples of a polynucleotide encoding an MEX1 protein to be expressed include (a) a polynucleotide encoding an MEX1 protein which comprises an amino acid sequence set forth in SEQ ID NO: 1 and is derived from *Arabidopsis thaliana* (the base sequence of such a polynucleotide is set forth in SEQ ID NO: 2); and a polynucleotide encoding an MEX1 protein which comprises an amino acid sequence set forth in SEQ ID NO: 3 and is derived from

*Chlamydomonas reinhardtii* (the base sequence of such a polynucleotide is set forth in SEQ ID NO: 4).

Specific examples of a polynucleotide encoding an MEX1 protein to be expressed also include:
(b) a polynucleotide encoding a polypeptide which comprises an amino acid sequence derived from the amino acid sequence set forth in SEQ ID NO: 1 or SEQ ID NO: 3 and maintaining the function of MEX1 wherein one or more amino acids are deleted, substituted, or added in the amino acid sequence; and
(c) a polynucleotide which is hybridizable with a polynucleotide comprising a base sequence complementary to that of the polynucleotide (a) or (b) under stringent conditions and encodes a polypeptide having the function of MEX1. Such polynucleotides (a) to (c) will be described below in more details.

Other specific examples of a polynucleotide encoding an MEX1 protein include a polynucleotide encoding an MEX1 protein which comprises an amino acid sequence set forth in SEQ ID NO: 17 and is derived from *Arabidopsis thaliana* (the base sequence of such a polynucleotide is set forth in SEQ ID NO: 18); and a polynucleotide encoding an MEX1 protein which comprises an amino acid sequence set forth in SEQ ID NO: 19 and is derived from *Chlamydomonas reinhardtii* (the base sequence of such a polynucleotide is set forth in SEQ ID NO: 20).

In another embodiment, the inventive alga preferably includes an ATG8 gene silenced. As used herein, the term "silencing" refers to decreasing the amount of a specific messenger RNA. "Silencing" encompasses transcriptional gene silencing and post-transcriptional gene silencing. Examples of the transcriptional gene silencing include epigenetic silencing, genomic imprinting, paramutation, transposon silencing, transgene silencing, and position effect. Examples of the post-transcriptional gene silencing include silencing using microRNA (miRNA), RNA interference, and nonsense mediated decay. The reduction of intracellular messenger RNA level is preferably determined if the intracellular messenger RNA level in an alga is 0.9 times or less, more preferably with at least 5% significant difference determined by t-test, as compared to that of a reference strain cultured under the same conditions.

Intracellular messenger RNA level in a reference strain is preferably measured at the same time and by the same method as that of an inventive alga, but may be determined based on accumulated background data. Intracellular messenger RNA level in an alga can be determined by any conventional technique such as real-time RT-PCR technique.

Examples of silencing applicable to the invention include silencing using miRNAs, i.e. low-molecular-weight RNAs produced from genes coding for primary transcripts of various sizes. A primary transcript (referred to as "pri-miRNA") is subjected to various nucleolytic steps to be processed into a shorter precursor miRNA or "pre-miRNA". The pre-miRNA is present in a folded form, and a resulting final (mature) miRNA is present in a form of duplex. The strands of the duplex are referred to as miRNAs (one of which eventually form a base pair with a target). The pre-miRNA is a substrate for a dicer that processes the precursor to generate a miRNA duplex. As with siRNA, one of the two strands of the miRNA duplex can be then incorporated into an RNA-induced splicing complex (RISC). A miRNA can be expressed by gene transfer. It binds to a target transcript sequence that is only partially complementary to the miRNA (see, for example, Zeng Y et al. (2002), Mol. Cell 9: 1327-1333) to inhibit translation of the target without affecting levels of non-target RNAs in the steady state (see, for example, Lee R C et al . (1993), Cell 75: 843-854; and Wightman B et al. (1993), Cell 75: 855-862). Examples of a miRNA applicable to the invention include artificial microRNAs (amiRNAs), i.e. molecules designed to induce silencing via the same mechanism as miRNAs. One of specific examples thereof is an amiRNA having the base sequence set forth in SEQ ID NO: 5.

An inventive alga with suppressed expression of ATG8 has increased production and/or accumulation of photosynthate as compared to that of a reference strain without suppression in expression of ATG8, and thus can allows algal biomass production with lower costs and higher efficiency than traditional methods.

The inventive alga preferably has both suppressed expression of ATG8 and increased chloroplastic glutathione concentration.

As used herein, "increased chloroplastic glutathione concentration" refers to a higher glutathione concentration in chloroplast as compared to that of a reference strain. The increase in chloroplastic glutathione concentration is preferably determined if the chloroplastic glutathione concentration in an alga is 1.1 times or more, more preferably with at least 5% significant difference determined by t-test, as compared to that of a reference strain cultured under the same conditions. The chloroplastic glutathione concentration of a reference strain is preferably measured at the same time and by the same method as that of an inventive alga, but may be determined based on accumulated background data.

The chloroplastic glutathione concentration of an alga can be directly measured by expressing roGFP2, i.e. a molecular probe that visualizes the redox state via redox-responsive changes in its fluorescence color, in chloroplast (see, for example, Meyer A J et al. (2007), Plant Journal 52: 973-986. Redox-sensitive GFP in *Arabidopsis thaliana* is a quantitative biosensor for the redox potential of the cellular glutathione redox buffer; and Gutscher M et al. (2009), Nat Methods 5: 553-559. Real-time imaging of the intracellular glutathione redox potential). Alternatively, the increase in glutathione concentration can be indirectly determined based on an increase in expression level of a protein involved in biosynthesis of glutathione or a polynucleotide encoding such a protein. Expression level of such a protein or polynucleotide can be appropriately measured by any conventional technique.

The "glutathione" includes reduced glutathione (hereinafter, referred to as "GSH") and oxidized glutathione (hereinafter, referred to as "GSSG"). In a method of the present invention, GSH and GSSG concentrations may be increased either alone or together.

The inventive alga preferably has increased chloroplastic expression and/or activity of at least one protein selected from the group consisting of γ-glutamylcysteine synthetase (hereinafter, also referred to as "GSH1"), glutathione synthetase (hereinafter, also referred to as "GSH2"), ATP sulfurylase, adenosine 5'-phosphosulfate reductase, sulfite reductase, cysteine synthase, and serine acetyltransferase. These proteins are involved in chloroplastic biosynthesis of glutathione, and an increased expression thereof indicate an increased chloroplastic glutathione concentration.

An inventive alga may further include a polynucleotide introduced therein and encoding at least one protein selected from the group consisting of GSH1, GSH2, ATP sulfurylase, adenosine 5'-phosphosulfate reductase, sulfite reductase, cysteine synthase, and serine acetyltransferase, in addition to a polynucleotide encoding MEX1 and/or a nucleic acid for silencing ATG8. An alga which includes such an exogenous polynucleotide introduced and expressed (overexpressed) therein has an increased chloroplastic glutathione concentration.

In other words, the present invention provides a transformed alga which includes a polynucleotide introduced therein and encoding at least one protein selected from the group consisting of GSH1, GSH2, ATP sulfurylase, adenosine 5'-phosphosulfate reductase, sulfite reductase, cysteine synthase, and serine acetyltransferase, in addition to a polynucleotide encoding MEX1 and/or a nucleic acid for silencing ATG8, and has increased chloroplastic glutathione concentration. Such a transformed alga naturally has an increased photosynthetic productivity.

Such a protein to be expressed in an alga or the polynucleotide encoding the protein may be from any origin if the protein or polynucleotide can be introduced or expressed to exert its action in the host alga, and may be either derived from the host alga, or from algae of other species than the host alga or from other plants. Preferred examples of the aforementioned proteins from other plant or polynucleotides encoding the proteins include those from a plant belonging to the genus *Arabidopsis* within the class Dicotyledoneae.

Specific examples of a polynucleotide encoding γ-glutamylcysteine synthetase to be expressed include (a) a polynucleotide encoding a γ-glutamylcysteine synthetase which comprises an amino acid sequence set forth in SEQ ID NO: 6 and is derived from *Chlamydomonas reinhardtii* (the base sequence of such a polynucleotide is set forth in SEQ ID NO: 7).

Specific examples of a polynucleotide encoding γ-glutamylcysteine synthetase to be expressed also include:
(b) a polynucleotide encoding a polypeptide which comprises an amino acid sequence derived from the amino acid sequence set forth in SEQ ID NO: 6 and maintaining the activity of γ-glutamylcysteine synthetase wherein one or more amino acids are deleted, substituted, or added in the amino acid sequence; and
(c) a polynucleotide which is hybridizable with a polynucleotide comprising a base sequence complementary to that of the polynucleotide (a) or (b) under stringent conditions and encodes a polypeptide having the activity of γ-glutamylcysteine synthetase. Such polynucleotides (a) to (c) will be described below in more details.

Introduction of such a polynucleotide in the cell of the inventive alga can be confirmed by any conventional technique such as PCR, southern hybridization, or northern hybridization. Alternatively, the introduction of the polynucleotide may also be confirmed by measuring expression of a protein encoded by the polynucleotide by any conventionally known immunological technique, or by measuring enzymatic activity of the protein encoded by the polynucleotide by any conventional biochemical technique.

An inventive alga with suppressed expression of ATG8 can achieve increased production and/or accumulation of photosynthate as compared to that of a reference strain. An inventive alga with both suppressed expression of ATG8 and increased chloroplastic glutathione concentration can achieve more increase in the production and/or accumulation of photosynthate as compared to that of a reference strain.

An alga with both suppressed expression of ATG8 and increased chloroplastic glutathione concentration can produce and/or accumulate photosynthate in a nitrogen-sufficient medium without requiring a nitrogen-deficient medium, which saves time and effort in replacement of the medium. Such an alga is also advantageous in that production and/or accumulation of photosynthate thereof can be readily enhanced by a mere slight improvement in light conditions.

Such an alga with both suppressed expression of ATG8 and increased chloroplastic glutathione concentration can cause extracellular transfer of photosynthate accumulated in the algal cell, which facilitates recovery of photosynthate. For example, if a photosynthate is starch, starch accumulated during photosynthesis can be transferred outside the cell as starch granules without requiring disruption of the algal cell. Accordingly, biomass production using an alga with suppressed expression of ATG8 and increased chloroplastic glutathione concentration enables relatively easy purification of starch.

The inventive alga increases facility and efficiency in induction of accumulation of photosynthate and/or recovery thereof, as compared to traditional techniques. Accordingly, use of the inventive alga in a method of biomass production that will be described below provides algal biomass production with lower costs and higher efficiency than traditional methods.

2. Starch Produced by an Inventive Alga

Starch granules produced by an inventive alga are characterized by a minute particle size. For example, general starch granules produced by plants such as corn, potato, and wheat have a mean particle size of 10 to 50 μm. In contrast, starch granules produced by the inventive alga are minute and uniform in size, with a mean particle size of 1.3 μm (S.D.: 0.181) in a major diameter and 1.0 μm (S.D.: 0.204) in a minor diameter. Starch granules produced by plants such as rice and quinoa are also minute, with a mean particle size of about 2 to 3 μm, but form an endosperm tissue via adhesion to each other, as in starch granules produced by plants such as corn, potato, and wheat. Accordingly, a costly process such as grinding is required for preparation of minute starch granules in a form of disaggregated particles from a raw material such as corn, potato, wheat, rice, or quinoa. Such minute starch granules are useful in production of pharmaceutical products. In other words, use of an inventive alga allows massive production of starch granules that are minute and uniform in size, and also enables a relatively easy purification thereof, via transfer of the produced starch granules outside the algal cell. Further, use of the inventive alga provides starch granules in a disaggregated form without requiring a process such as grinding.

As explained above, starch granules produced by the inventive alga are minute as compared to general starch granules produced by plants such as corn, potato, or wheat. Such minute starch granules are useful in production of pharmaceutical products. Specifically, such minute starch granules have a particle size smaller than a diameter of bronchioles in lungs, and will be a promising carrier for delivering a therapeutic agent for a lung disease to the bronchioles (dry powder inhaler containing a therapeutic agent combined with minute starch granules).

Such minute starch granules are also expected to be used in a form of so-called "edible vaccine", i.e. a peptidic antigen associated with the starch granule surface (for example, Dauvillee D et al. (2010) PLoS ONE 5(12): e15424; and Japanese Unexamined Patent Application Publication (Translation of PCT Application) No. 2003-500060 (Japanese Patent Application No. 2000-620111) disclose genetically engineered starch granules produced in *Chlamydomonas* and containing a malarial antigen associated on their surface.

3. Inventive Method of Producing Modified Alga

An inventive method of producing an alga produces the aforementioned modified alga with suppressed intracellular expression of ATG8 and increased photosynthetic productivity as compared to that of a reference strain (i.e. the inventive alga). The inventive method involves at least an ATG8 expression suppressing step to suppress expression of ATG8 in the algal cell, and may involve any other step and may be practiced under a variety of conditions.

The inventive method of producing a modified alga will now be described in detail.

(1) ATG8 Expression Suppressing Step

The ATG8 expression suppressing step suppresses the expression of ATG8 in an alga.

The expression "suppress the expression of ATG8" refers to reducing the expression of ATG8 in an alga as compared to that of a reference strain. In other words, an alga after the ATG8 expression suppressing step has decreased expression of ATG8 as compared to that of a reference strain. The reduction in expression of ATG8 in an alga as compared to that of a reference strain can be determined by a method described in the section explaining the inventive alga.

In the ATG8 expression suppressing step, expression of ATG8 may be suppressed by any method that can produce an alga with decreased expression of ATG8. Examples of such a method include (i) random mutagenesis in the alga and (ii) introduction of a substance which suppresses the expression of ATG8 into the algal cell (or into the algal genome, in some cases).

The methods (i) and (ii) are now described in detail.

(i) Random Mutagenesis in an Alga

Random mutation may be introduced in an alga by any method appropriately selected from known techniques. Specific examples of the method for random mutagenesis include chemical treatment of an alga (with EMS or NTG, for example), radioactive mutagenesis, transposon mutagenesis, T-DNA mutagenesis, mutagenesis using prokaryotic-eukaryotic cell conjugation, and physical gene transfer using a gene gun, for example. For example, mutation may be introduced into an ATG8 gene or a gene encoding a protein which positively controls the expression of ATG8 by such a method, so as to decrease the expression of ATG8. Alternatively, mutation may be introduced into a gene encoding a protein which negatively controls the expression of ATG8 by any of the methods described above, so as to increase the activity of the protein to decrease the expression of ATG8.

Algae with desired mutation may be screened by any known method. Examples of the screening method include selection of mutant algae with suppressed expression of ATG8 based on the direct measurement of intracellular expression of ATG8 as described above, and selection of mutant algae with increased expression and/or activity of MEX1 protein.

(ii) Introduction of Substance which Suppresses Expression of ATG8 into Cell

A modified alga with decreased intracellular expression of ATG8 can also be produced by introducing the "substance which suppresses intracellular expression of ATG8" as described above, such as (A) a polynucleotide encoding a protein which suppresses expression of ATG8 or (B) a polynucleotide having a function of silencing the ATG8 gene, for example. Such polynucleotides (A) and (B) may be used either alone or in combination.

As used herein, the term "polypeptide" is interchangeable with the terms "peptide" or "protein". As used herein, the term "polynucleotide" is interchangeable with the term "gene", "nucleic acid" or "nucleic acid molecule" and refers to a nucleotide polymer.

The "introduction of a polynucleotide" refers to any process that allows an intended polynucleotide to be included in the algal cell, and include insertion (introduction) of the intended polynucleotide in an algal genome. Successful introduction of a polynucleotide in an algal cell can be confirmed by any conventional technique such as PCR, southern hybridization, or northern hybridization.

Introduction of at least one polynucleotide (A) into an algal cell increases the expression of a protein which suppresses intracellular expression of ATG8, resulting in suppressed expression of ATG8 in the cell.

Preferred examples of such a polynucleotide include a polynucleotide encoding MEX1 (hereinafter, also referred to as "MEX1 gene"). Such a polynucleotide is preferably from a plant, more preferably from the host alga, but polynucleotides from algae other than the host alga or from higher plants may also be suitably used.

The "MEX1 gene" is not limited to specific genes. Examples of MEX1 genes preferred in the invention include the MEX1 gene of *Chlamydomonas* used by the inventors in the Examples. *Chlamydomonas* MEX1 has the amino acid sequence set forth in SEQ ID NO: 1, and a gene (full-length cDNA) encoding it has the base sequence set forth in SEQ ID NO: 2.

Another example of MEX1 genes preferred in the invention is the MEX1 gene of *Arabidopsis thaliana* used by the inventors in the Examples. MEX1 of *Arabidopsis thaliana* has the amino acid sequence set forth in SEQ ID NO: 3, and a gene (full-length cDNA) encoding it has the base sequence set forth in SEQ ID NO: 4.

In summary, preferred examples of the nucleotide to be introduced in an alga in the invention include the following polynucleotides (a) to (c):

(a) a polynucleotide encoding a polypeptide which comprises an amino acid sequence set forth in SEQ ID NO: 1 or SEQ ID NO: 3;

(b) a polynucleotide encoding a polypeptide which includes an amino acid sequence derived from the amino acid sequence set forth in SEQ ID NO: 1 or SEQ ID NO: 3 and maintaining the function of MEX1 wherein one or more amino acids are deleted, substituted, or added in the amino acid sequence; and (c) a polynucleotide which is hybridizable with a polynucleotide comprising a base sequence complementary to that of the polynucleotide (a) or (b) under stringent conditions and encodes a polypeptide having the function of MEX1.

The expression "deletion, substitution, or addition of one or more amino acids" refers to deletion, substitution, or addition of any number of amino acids that can be involved in deletion, substitution, or addition by a known technique of producing a mutant peptide, such as site-specific mutagenesis (preferably ten or less, more preferably seven or less, yet more preferably five or less amino acids). Such a mutant protein includes not only proteins having mutation artificially introduced by a known technique of producing a mutant polypeptide but also proteins isolated and purified from naturally-occurring proteins.

It is well-known in the art that one or more amino acids in an amino acid sequence of a protein may be readily modified without any significant influence on its original structure or function. It is also well-known that mutant proteins include not only artificially modified proteins but also naturally-occurring mutant proteins that substantially maintain the structure and function of the original protein.

Preferred mutants have conservative or non-conservative amino acid substitution, deletion, or addition, preferably silent substitution, addition, or deletion. Conservative substitution is particularly preferred. Such mutation does not change the polypeptide activity in the present invention.

Typical conservative substitutions include the following substitutions: one substitution among aliphatic amino acids, i.e. Ala, Val, Leu, and Ile; substitution among hydroxyl residues, i.e. Ser and Thr; substitution among acidic residues, i.e. Asp and Glu; substitution among amido residues, i.e. Asn and Gln; substitution among basic residues, i.e. Lys and Arg; and substitution among aromatic residues, i.e. Phe and Tyr.

As used herein, the term "stringent conditions" refers to conditions where polynucleotides hybridize with each other only if they have sequence identity of at least 90%, preferably at least 95%, most preferably at least 97%. Specific examples of such conditions include conditions involving overnight incubation in a hybridization solution (containing 50% formamide, 5×SSC (150 mM NaCl, 15 mM trisodium citrate), 50 mM sodium phosphate (pH: 7.6), 5× Denhardt's solution, 10% dextran sulfate, and 20 µg/ml denatured, sheared salmon sperm DNA) at 42° C., followed by washing of the filter in 0.1×SSC at about 65° C.

Hybridization can be carried out by any well-known technique such as the method described in Sambrook J et al. (2001), Molecular Cloning, A Laboratory Manual, 3rd Ed., Cold Spring Harbor Laboratory. In general, a higher temperature or lower salt concentration increases stringency (i.e. decreases the probability of hybridization). As a result, hybridization under higher stringency provides a polynucleotide with higher homology.

The identity of amino acid sequences or base sequences can be determined using the BLAST algorithm as described by Karlin and Altschul (Karlin S, Altschul S F (1990), Proc. Natl. Acad. Sci. USA 87: 2264-2268; and Karlin S, Altschul S F (1993), Proc. Natl. Acad. Sci. USA, 90: 5873-5877). Programs based on the BLAST algorithm, such as BLASTN and BLASTX, have also been developed (Altschul S F et al. (1990), J. Mol. Biol. 215: 403-410).

MEX1 genes from other plants than *Chlamydomonas* may also be suitably used in the invention. Known examples of such MEX1 genes include those from *Arabidopsis thaliana* (TAIR Accession Gene: 2157491; Name: AT5G17520.1), *Glycine max* (NCBI Reference Sequence: XP_003539988), *Oryza sativa* (Genbank accession: AGR54532.1), and *Malus domestica* (Genbank accession: DQ648082.1).

Alternatively, introduction of the aforementioned polynucleotide (B) into an algal cell can decrease expression of ATG8 in the cell. Examples of such a polynucleotide include double-stranded RNAs (dsRNAs), small interfering RNAs (siRNAs), template DNAs for these RNAs, and microRNAs (miRNAs), as used in a conventional RNA interference (RNAi) technique. Such polynucleotides inhibit transcription and/or translation of an ATG8 gene, for example.

Preferred examples of the miRNA usable in the invention include, but are not limited to, the miRNA of SEQ ID NO: 5.

"The polynucleotide" used in the inventive method of producing a modified alga may be a DNA from a genomic DNA or a cDNA, a chemically synthesized DNA, or an RNA, and may be appropriately selected depending on the purpose.

If a polynucleotide used in the inventive method of producing a modified alga is, for example, an MEX1 gene, examples of a method of preparing the polynucleotide include isolating and cloning a DNA fragment encoding MEX1 by a known technique. In such a case, a probe is prepared which can specifically hybridize with a partial base sequence of a DNA encoding *Chlamydomonas* MEX1, and a genomic DNA library or cDNA library is screened with the probe.

Alternatively, a polynucleotide used in the inventive method of producing a modified alga may be prepared by an amplification technique such as PCR. For example, an MEX1 gene may be prepared by designing a set of primers based on 5'- and 3'-terminal sequences (or complementary sequences thereof), respectively, of a cDNA encoding *Chlamydomonas* MEX1; and carrying out a process such as PCR with the primer set using a genomic DNA (or cDNA) as template, to amplify a DNA region between the primers. Such a method allows large-scale preparation of MEX1-encoding DNA fragments (MEX1 gene) used in the invention.

The polynucleotide used in the inventive method of producing a modified alga may be derived from a desired algal or plant source.

In the inventive method of producing a modified alga, a polynucleotide may be introduced in an alga by any process. For example, a polynucleotide may be introduced in an algal cell by introduction of an expression vector including the polynucleotide. Such an expression vector may be constructed by any conventional technique. For example, "Japanese Unexamined Patent Application Publication No. 2007-43926" and "Japanese Unexamined Patent Application Publication No. 10-0570868" disclose methods for construction of an expression vector and transformation of algae. In accordance with such methods, a recombinant expression vector can be constructed by ligating a promoter and a terminator that act in an algal cell to the upstream and downstream, respectively, of a polynucleotide to be introduced, and then introduced into the algal cell.

Preferred examples of such a "promoter" include the Hsp70A/RBc_S2 promoter that has been broadly used for gene expression in algae and provides high constitutive expression of transcripts or proteins encoded by a polynucleotide to be introduced.

(2) Glutathione Enriching Step

The inventive method of producing a modified alga preferably further involves a glutathione enriching step to increase the chloroplastic glutathione concentration of the alga.

As used herein, the expression "to increase the chloroplastic glutathione concentration" refers to increasing a chloroplastic glutathione concentration in an alga as compared to that of a reference strain. In other words, an alga after the glutathione enriching step has a higher glutathione concentration than that of a reference strain. The increase in the chloroplastic glutathione concentration of the alga as compared to that of the reference strain can be determined by a method described in the section explaining the inventive alga.

In the glutathione enriching step, a chloroplastic glutathione concentration maybe increased by any process that can provide the resulting alga with an increased chloroplastic glutathione concentration. Examples of such a method include the same methods as in the ATG8 expression suppressing step and the method described in PTL 5, including (i) random mutagenesis in an alga of interest by a known mutagenesis technique; and (ii) introduction of a substance which increases the chloroplastic glutathione concentration into the algal cell (or into the algal genome, in some cases).

(i) Random Mutagenesis in an Alga

Random mutation may be introduced in an alga by any one appropriately selected from known techniques. Specific examples of the technique for random mutagenesis include chemical treatment of an alga (with EMS or NTG, for example), radioactive mutagenesis, transposon mutagenesis, T-DNA mutagenesis, mutagenesis using prokaryotic-eukaryotic cell conjugation, and physical gene transfer using a gene gun, for example. For example, mutation is introduced into a polynucleotide encoding a protein involved in the glutathione biosynthetic pathway in the chloroplast, such as GSH1, GSH2, ATP sulfurylase, adenosine 5'-phosphosulfate reductase, sulfite reductase, cysteine synthase, or serine acetyltransferase, so as to increase the expression and/or activity of the protein, which provides the resulting alga with an increased chloroplastic glutathione concentration.

Algae with desired mutation may be screened by any known method. Examples of the screening method include selection of mutant algae with an increased glutathione concentration based on the direct measurement of the chloroplastic glutathione concentration as described above, and selection of mutant algae with increased expression and/or activity of a protein such as GSH1, GSH2, ATP sulfurylase, adenosine 5'-phosphosulfate reductase, sulfite reductase, cysteine synthase, or serine acetyltransferase.

(ii) Introduction of Substance which Increases a Chloroplastic Glutathione Concentration into Cell A modified alga with an increased chloroplastic glutathione concentration can also be produced by introducing the "substance which increases a chloroplastic glutathione concentration" as described above, such as (A) a polynucleotide encoding a protein which increases a chloroplastic glutathione concentration in an alga; or (B) a polynucleotide having a function of suppressing expression of a protein which decreases a chloroplastic glutathione concentration in an alga. Such polynucleotides (A) and (B) may be used either alone or in combination.

Introduction of at least one polynucleotide (A) into an algal cell increases expression of a protein which increases a chloroplastic glutathione concentration, resulting in an increased chloroplastic glutathione concentration.

Preferred examples of such a polynucleotide include a polynucleotide encoding γ-glutamylcysteine synthetase (hereinafter, also referred to as "GSH1 gene"), a polynucleotide encoding glutathione synthetase (hereinafter, also referred to as "GSH2 gene"), a polynucleotide encoding ATP sulfurylase, a polynucleotide encoding adenosine 5'-phosphosulfate reductase, a polynucleotide encoding sulfite reductase, a polynucleotide encoding cysteine synthase, and a polynucleotide encoding serine acetyltransferase. Such polynucleotides are preferably from a plant, more preferably from the host alga, but polynucleotides from algae other than the host alga or from higher plants may also be suitably used.

The "γ-glutamylcysteine synthetase (GSH1)" is an enzyme that catalyzes combination of cysteine with glutamate at the γ-position of glutamate through an amido bond, to synthesize γ-glutamylcysteine. The "glutathione synthetase (GSH2)" is an enzyme that catalyzes binding of glycine to γ-glutamylcysteine to synthesize glutathione.

The "GSH1 gene" is not limited to specific genes. Examples of GSH1 gene preferred in the invention include the GSH1 gene of *Chlamydomonas* (CHLRE-DRAFT_181975) used by the inventors in the Examples. The *Chlamydomonas* GSH1 has the amino acid sequence set forth in SEQ ID NO: 6, and a gene (full-length cDNA) encoding it has the base sequence set forth in SEQ ID NO:

7. Translation products of the GSH1 gene of *Chlamydomonas* include a chloroplast targeting signal peptide in the N-terminal region. Thus, the translation products of the GSH1 gene from *Chlamydomonas*, i.e. *Chlamydomonas* GSH1, are normally present in the chloroplast.

In summary, preferred examples of the nucleotide to be introduced in an alga in the invention include the following polynucleotides (a) to (d):
(a) a polynucleotide encoding a polypeptide which comprises an amino acid sequence set forth in SEQ ID NO: 6;
(b) a polynucleotide encoding a polypeptide which comprises an amino acid sequence derived from the amino acid sequence set forth in SEQ ID NO: 6 and maintaining the γ-glutamylcysteine synthetase activity wherein one or more amino acids are deleted, substituted, or added in the amino acid sequence; and
(c) a polynucleotide which is hybridizable with a polynucleotide comprising a base sequence complementary to that of the polynucleotide (a) or (b) under stringent conditions and encodes a polypeptide having γ-glutamylcysteine synthetase activity.

As used herein, the "γ-glutamylcysteine synthetase activity" refers to activity of catalyzing a reaction that forms an amido bond between cysteine and the γ-position of glutamate. The "γ-glutamylcysteine synthetase activity" can be measured by the following method, for example: algal cell lysate is centrifuged and the supernatant is collected as a sample; the sample is added to a reaction solution containing cysteine, glutamate, and ATP; and the amount of γ-glutamylcysteine synthesized in a certain period of time is measured. Such measurement is carried out under conditions with an anti-oxidant measure, such as purging the solution with nitrogen. Alternatively the γ-glutamylcysteine synthetase activity may be measured by determining the amount of phosphoric acid generated the reaction.

GSH1 genes from other plants than *Chlamydomonas* may also be suitably used in the invention. Known examples of such GSH1 genes include those from *Arabidopsis thaliana* (TAIR Accession Gene: 2127172; Name AT4G23100.1), *Zinnia elegans* (Genbank accession: AB158510), *Oryza sativa* (Genbank accession: AJ508915), and *Nicotiana tabacum* (Genbank accession: DQ444219). Translation products of these genes also include a chloroplast targeting signal peptide in the N-terminal region, as in the case of *Chlamydomonas*.

Alternatively, introduction of the aforementioned polynucleotide (B) into an algal cell can decrease expression of a protein which decreases a chloroplastic glutathione concentration, resulting in an increased chloroplastic glutathione concentration. Examples of such a polynucleotide include double-stranded RNAs (dsRNAs), small interfering RNAs (siRNAs), and template DNAs for these RNAs, as used in a conventional RNA interference (RNAi) technique.

Preferred examples of the "protein which decreases a chloroplastic glutathione concentration in an alga" include CLT1. The "CLT1" is a transporter that delivers glutathione from the chloroplast to the cytoplasm. The transporter was first found in *Arabidopsis thaliana* and designated "CLT1" (see Maughan S C et al. (2010), Proc. Natl. Acad. Sci. USA 107 (5): 2331-2336). Accordingly, examples of the polynucleotide (B) include polynucleotides intended to decrease expression of a glutathione transporter, such as CLT1.

(3) Additional Steps

The inventive method of producing a modified alga may involve a screening step to screen modified algae with suppressed intracellular expression of ATG8, in addition to the "ATG8 expression suppressing step" described above.

The inventive method of producing a modified alga may also involve a screening step to screen modified algae with an increased chloroplastic glutathione concentration in addition to the "glutathione enriching step" described above.

For example, transformed algae after introduction of a gene of interest may be first screened by a conventional chemical screening test based on expression of a drug-resistant marker, such as kanamycin-resistant or hygromycin-resistant marker. The screened algae may be then tested to confirm whether the gene of interest has been successfully introduced therein, by a technique such as PCR, southern hybridization, or northern hybridization. For example, successful transformation can be confirmed in the following steps of: preparing DNA from a transformed alga; designing primers specific to the DNA that has been introduced into the alga; carrying out PCR; subjecting the amplification products to electrophoresis, such as agarose gel electrophoresis, polyacrylamide gel electrophoresis, or capillary electrophoresis; and staining the resulting gel with ethidium bromide, for example, to detect the amplification product of interest.

Transformed algae with suppressed intracellular expression of ATG8 may be screened by the measurement of intracellular expression of ATG8 as described above, for example. Individuals with an increased chloroplastic glutathione concentration may be screened by the measurement of chloroplastic glutathione concentration as described above, for example.

4. Inventive Method of Biomass Production

The inventive method of biomass production produces biomass using a modified alga produced by the aforementioned method of producing a modified alga which has suppressed intracellular expression of ATG8 or which has both suppressed expression of ATG8 and increased chloroplastic glutathione concentration, as compared to a reference strain.

The modified alga and the method of producing a modified alga according to the invention have been explained above in the sections "Inventive alga" and "Inventive method of producing modified alga", respectively, and redundant description will be eliminated.

As used herein, the term "biomass" refers to substances produced by algae through photosynthetic carbon fixation, including saccharides (for example, starch) and oils and fats, for example, and is interchangeable with "photosynthate".

According to the inventive method of biomass production, production or accumulation of photosynthate in the algal cell maybe induced by any method. For example, the inventive method of biomass production may involve a photoirradiation step to irradiate the alga with light for inducing production or accumulation of photosynthate in the algal cell.

(1) Photoirradiation Step
(i) Modified Alga with Suppressed Expression of ATG8

A modified alga which has suppressed expression of ATG8 but does not have an increased chloroplastic glutathione concentration (modified alga with suppressed ATG8 expression) is preferably cultured under a nitrogen-deficient condition for inducing accumulation of photosynthate in the algal cell. The term "nitrogen-deficient condition" refers to culture in a culture medium having an inorganic nitrogen content of less than 0.001% by weight (calculated as nitrogen atom concentration). The term "inorganic nitrogen" refers to nitrogen such as ammonia nitrogen, nitrite nitrogen, and nitrate nitrogen, for example. A non-limiting example of a nitrogen-free culture medium preferred in the invention is a TAP N-free medium. It has substantially the same composition as a known TAP medium, but does not contain a nitrogen source. The TAP culture medium is mainly composed of tris(hydroxymethyl)aminomethane (Tris), acetate, and phosphate, and contains ammonium chloride (0.4 g/l) as a nitrogen source. Its detailed composition is described in Fukuzawa H and Kubo T (2009), Teion Kagaku (Low Temperature Science) 67: 17-21. The TAP N-free culture medium has substantially the same composition as the TAP culture medium, except that it contains 0.4 g/l of potassium chloride instead of ammonium chloride.

If a polynucleotide having a function of silencing an ATG8 gene is used for suppressing expression of ATG8, such a culture medium preferably contain the polynucleotide. The concentration of the polynucleotide in the culture medium is preferably 10 µg/ml, more preferably 4 µg/ml, for example.

The sequence of the polynucleotide having a function of silencing an ATG8 gene can be designed by a known technique. For example, the sequence set forth in SEQ ID NO: 5 can be used suitably. The polynucleotide having a function of silencing an ATG8 gene can be incorporated in a genome of a target alga in combination with a suitable promoter, so that it is expressed and acts in the target alga. Alternatively, the polynucleotide may be added to a culture medium under suitable conditions to exert the function thereof.

Induction of accumulation of photosynthate does not require adjustment of light intensity for irradiation of an alga, but the light intensity may be 40 $E/m^2/sec$ or more, for example, preferably 50 $\mu E/m^2/sec$ or more, more preferably 60 $\mu E/m^2/sec$ or more, yet more preferably 70 $\mu E/m^2/sec$ or more, 80 $\mu E/m^2/sec$ or more, 90 $\mu E/m^2/sec$ or more, or 100 $\mu E/m^2/sec$ or more; and is preferably 1000 $\mu E/m^2/sec$ or less, for example, more preferably 500 $\mu E/m^2/sec$ or less, yet more preferably 100 $\mu E/m^2/sec$ or less.

Irradiation with light within such a range requires no special photoirradiation device. Examples of the light include sunlight; sunlight qualitatively and quantitatively adjusted with a mirror, optical fiber, filter, or mesh, for example; artificial light such as light from an incandescent lamp, fluorescent lamp, mercury lamp, or light-emitting diode. The light for irradiation may have a wavelength in a region suitable for photosynthesis in general algae, preferably 400 nm to 700 nm, for example.

Alternatively, the photoirradiation step may be carried out under an autotrophic condition. As used herein, the "autotrophic condition" refers to a condition of culturing without supply of a carbon source other than carbon dioxide. In detail, the photoirradiation step may be carried out under an autotrophic condition by irradiating an inventive alga with light in an HSM culture medium under supply of atmospheric air, for example. The source of carbon dioxide is not limited to the atmospheric air. Carbon dioxide contained in flue of thermal power stations or ironworks can also be supplied to a culture medium at a higher concentration than in the atmospheric air, which allows increased productivity.

Under an autotrophic condition, carbon dioxide or gas containing carbon dioxide is transmitted from near the bottom of a culture vessel (i.e. passed through the solution). Carbon dioxide diffuses in water at a rate much lower than in the atmospheric air, which requires stirring the culture medium to achieve uniform irradiation of the alga. Carbon dioxide dissolves in water to form anions. A culture medium with low buffer capacity is rendered more acidic by the bubbling to decrease the solubility of carbon dioxide, resulting in a lower consumption rate of carbon dioxide in photosynthesis. Thus, the culture medium preferably has buffer capacity sufficient for maintaining its pH value within a neutral to alkaline pH range. Preferred examples of such a medium include conventional HSM medium.

(ii) Modified Alga with Suppressed Expression of ATG8 and Increased Glutathione Concentration A modified alga which has both suppressed expression of ATG8 and increased chloroplastic glutathione concentration (modified alga with suppressed ATG8 expression and increased glutathione concentration) is not required to be cultured under the nitrogen-deficient condition for inducing accumulation of photosynthate in the algal cell. Thus, the photoirradiation step described above may be carried out under a condition without nitrogen deficiency. As used herein, the "condition without nitrogen deficiency" refers to culture in a culture medium having an inorganic nitrogen content necessary for growth of algae. The inorganic nitrogen content in a culture medium necessary for growth of algae is 0.001% to 0.1% by weight (calculated as nitrogen atom concentration), preferably 0.005% to 0.05% by weight. The TAP medium used in the Examples below has an inorganic nitrogen content of approximately 0.01% by weight (calculated as nitrogen atom concentration).

Non-limiting examples of a culture medium having an inorganic nitrogen content necessary for the growth of an alga with suppressed expression of ATG8 and increased glutathione concentration include culture media which are normally used in culturing algae, such as traditional TAP medium, HSM medium, and ATCC897 medium.

Induction of accumulation of photosynthate does not require adjustment of light intensity for irradiation of the alga, but the light intensity may be 1000 $\mu E/m^2/sec$ or less, for example, preferably 500 $\mu E/m^2/sec$ or less, more preferably 400 $\mu E/m^2/sec$ or less, 300 $\mu E/m^2/sec$ or less, 200 $\mu E/m^2/sec$ or less, 150 $\mu E/m^2/sec$ or less, 100 $\mu E/m^2/sec$ or less, or 80 $\mu E/m^2/sec$ or less. A lower light intensity for irradiation increases energy efficiency, resulting in increased productivity. The modified alga with suppressed expression of ATG8 and increased glutathione concentration is advantageous in that it can produce photosynthate inside and outside the cell under a lower light intensity than traditional wild-type algae. The lower limit of the light intensity for irradiation may be any value, for example, may be 40 $\mu E/m^2/sec$, which can be set as a practical value.

Examples of a photoirradiation device for irradiation with light within such a range include those described above in case (i).

In one embodiment, the modified alga with suppressed ATG8 expression and increased glutathione concentration may be cultured in a TAP medium under irradiation with light of 45 $\mu E/m^2/sec$ to induce accumulation of starch in the cell. In another embodiment, the modified alga with suppressed ATG8 expression and increased glutathione concentration may be cultured in a TAP medium under irradiation with light of 80 $\mu E/m^2/sec$ to induce accumulation of starch in the cell.

The photoirradiation step of the modified alga with suppressed expression of ATG8 and increased glutathione concentration may be carried out under the nitrogen-deficient condition explained above in case (i). In one embodiment, the modified alga with suppressed expression of ATG8 and increased glutathione concentration may be cultured in the nitrogen-deficient condition (i.e. in the TAP N-free medium) under photoirradiation with light of 80 $\mu E/m^2/sec$ to induce accumulation of starch in the cell.

As described above, the modified alga with suppressed expression of ATG8 and increased glutathione concentration is characterized in that it does not require any step of nutrient restriction, such as step of providing nitrogen-deficient condition, for inducing production of photosynthate. In other words, in one embodiment of the invention using the modified alga with suppressed expression of ATG8 and increased glutathione concentration, the method may be practiced substantially without carrying out a nutrient restriction step, such as a step of providing a nitrogen-deficient condition (i.e. such a method involves substantially no nutrient restriction step). Such a feature simplifies the process, resulting in increased photosynthetic productivity.

Alternatively, the photoirradiation step may be carried out under the autotrophic condition explained above in case (i).

(2) Additional Step

The inventive method of biomass production may further involve a step of recovering photosynthate in addition to the aforementioned "photoirradiation step".

(i) Modified Alga with Suppressed Expression of ATG8

If a modified alga which has suppressed expression of ATG8 but does not have increased chloroplastic glutathione concentration (modified alga with suppressed ATG8 expression) is used in the inventive method of biomass production, starch granules may be recovered by lysing the cell and then subjecting the lysate to a separation procedure, such as leaving the lysate to stand for spontaneous precipitation, centrifugation, or sieving. The separation procedure may be selected based on physical properties of the starch granules and the algal cell lysate, such as particle size and/or specific gravity.

(ii) Modified Alga with Suppressed Expression of ATG8 and Increased Glutathione Concentration If a modified alga which has both suppressed expression of ATG8 and increased chloroplastic glutathione concentration (modified alga with suppressed expression of ATG8 and increased glutathione concentration) is used in the inventive method of biomass production, the cell can be induced to export the starch accumulated therein outside the cell in the form of starch granules. If the photosynthate is starch, the step of recovering photosynthate may be practiced by separating the exported starch granules from the alga and recovering the separated starch granules. The exported starch granules may be separated from the alga by any method, including a separation procedure such as standing for spontaneous precipitation, centrifugation, or sieving. The separation procedure may be selected based on physical properties of the starch granules and the algal cell lysate, such as particle size and/or specific gravity.

In the inventive method of biomass production, in either of cases (i) and (ii), use of the inventive alga or an alga produced by the inventive method of producing a modified alga increases the facility and efficiency in both inducing accumulation of photosynthate and recovery of the photosynthate, as compared to traditional techniques. Accordingly, the inventive method of biomass production provides algal biomass production with lower costs and higher efficiency than traditional methods.

The invention should not be construed to the aforementioned embodiments. Various modifications are possible within the scope of the claims, and embodiments formed by appropriately combining technical features disclosed in different embodiments are also encompassed within the technical scope of the invention.

EXAMPLES

The present invention will now be described in more details by way of Examples, but should not be construed to be limited to the Examples.

Example 1

Production of Modified Algae

<Production of Modified Strain with Suppressed Expression of ATG8: 1>

The MEX1 gene (SEQ ID NO: 4) encoding the MEX1 protein from *Chlamydomonas reinhardtii* (SEQ ID NO: 3; hereinafter, referred to as "CrMEX1") was ligated to the downstream of the Hsp70A/RBc_S2 promoter to prepare a plasmid.

Specific procedure was as follows: A circular DNA vector for *Chlamydomonas*, pChlamy1 (available from Life Technologies Corporation) was sequentially treated with restriction enzymes Kpn I and Not I to be cleaved (DNA fragment 1). A polynucleotide (about 1.7 kbp) consisting of nucleotides 163 to 1830 of the sequence set forth in SEQ ID NO: 8 was prepared by the following method.

*Chlamydomonas reinhardtii* CC-503 strain (supplied from *Chlamydomonas* Genetics Center at Duke University, US) was cultured in a TAP medium for four days at 24° C. and under irradiation with light with an intensity of 50 $\mu E/m^2/sec$. The cells were then collected from the culture, and a cDNA mixture was prepared from the cells using a cDNA synthesis reagent kit (Solid phase cDNA synthesis kit; available from TAKARA BIO INC.). The cDNA mixture was used as a template, and was subjected to PCR with oligonucleotides having sequences of SEQ ID NO: 9 and SEQ ID NO: 10, respectively, in accordance with a known technique (annealing temperature: 68° C.). A *Chlamydomonas* MEX1 gene was thereby collected as a polynucleotide of about 1.7 kbp including the ORF followed by the 3'UTR region. The polynucleotide was further treated with the restriction enzymes Kpn I and Not I to process its terminal structure (DNA fragment 2).

The DNA fragments 1 and 2 were ligated or recircularized to each other. The circular DNA was amplified with *Escherichia coli*, and the amplification products were extracted from *E. coli* and were purified, in accordance with a known technique.

This procedure generated the base sequence set forth in SEQ ID NO: 8 in the circular DNA molecule. In the base sequence of SEQ ID NO: 8, nucleotides 1 to 3 form the start codon, and nucleotides 1286 to 1288 form the stop codon. In other words, the *Chlamydomonas* MEX1 gene includes nucleotides 1 to 1288 of the base sequence set forth in SEQ ID NO: 8 as the open reading frame (ORF). Nucleotides 9 to 153 of the base sequence form an intron sequence.

The resulting plasmid including the polynucleotide for Hsp70A-Rbc_S2 promoter-CrMEX1 was linearized with a restriction enzyme Sca I, and the linearized plasmid was introduced in the *Chlamydomonas reinhardtii* CC-503 strain by glass beads technique (see Kindle K L (1990), Proc. Natl. Acad. Sci. USA 87: 1228-1232). The transformed strain was screened to select a strain which included the polynucleotide inserted in the genomic DNA and exhibited stable inheritance of the polynucleotide to the next generation through the cell replication. The screening was based on the exhibition of hygromycin resistance by the transformed CC-503 strain. Insertion of the plasmid DNA including the polynucleotide into the genomic DNA was confirmed by PCR technique.

The produced algal strain with overexpression of CrMEX1 is referred to as "modified strain with suppressed expression of ATG8 (CC-503/CrMEX1ox)".

<Production of Modified Strain with Suppressed Expression of ATG8: 2>

An MEX1 gene (SEQ ID NO: 2) encoding the MEX1 protein from *Arabidopsis thaliana* (SEQ ID NO: 1; hereinafter, referred to as "AtMEX1") was ligated to the downstream of the Hsp70A/RBc_$_S$2 promoter to prepare a plasmid.

Specific procedure was as follows: A circular DNA vector for *Chlamydomonas*, pChlamy3 (available from Life Technologies Corporation) was sequentially treated with restriction enzymes Kpn I and Not I to be cleaved (DNA fragment 3). A polynucleotide (about 1.3 kbp) consisting of nucleotides 163 to 1442 of the sequence set forth in SEQ ID NO: 11 was prepared by the following method.

*Arabidopsis thaliana*, Columbia strain was grown for three weeks at 22° C. under diurnal conditions with a light period (100 $\mu E/m^2/sec$) of 16 hours and a dark period of eight hours. A cDNA mixture was prepared from the plant as in <Production of modified strain with suppressed expression of ATG8: 1>. The cDNA mixture was used as a template, and was subjected to PCR with oligonucleotides having sequences of SEQ ID NO: 12 and SEQ ID NO: 13 in accordance with a known technique (annealing temperature: 68° C.). The ORF of the *Arabidopsis thaliana* MEX1 gene was thereby collected as a polynucleotide of about 1.3 kbp. The polynucleotide was further treated with the restriction enzymes Kpn I and Not I to process its terminal structure (DNA fragment 4).

The DNA fragments 3 and 4 were ligated or recircularized to each other. The circular DNA was amplified in *Escherichia coli*, and the amplification products were extracted from *E. coli* and were purified, in accordance with a known technique.

This procedure generated the base sequence set forth in SEQ ID NO: 11 in the circular DNA molecule. In the base sequence of SEQ ID NO: 11, nucleotides 1 to 3 form the start codon, and nucleotides 1412 to 1414 form the stop codon. In other words, the *Arabidopsis thaliana* MEX1 gene includes nucleotides 1 to 1414 of the base sequence set forth in SEQ ID NO: 11 as the open reading frame (ORF). Nucleotides 9 to 153 of the base sequence form an intron sequence.

The prepared plasmid including the polynucleotide for Hsp70A-Rbc_S2 promoter-AtMEX1 was linearized with a restriction enzyme Sca I, and the linearized plasmid was introduced in the *Chlamydomonas reinhardtii* CC-503 strain by glass beads technique (see Kindle K L (1990), Proc. Natl. Acad. Sci. USA 87: 1228-1232). The transformed strain was screened to select a strain which included the polynucleotide inserted in the genomic DNA and exhibited stable inheritance of the polynucleotide to the next generation through the cell replication. The screening was based on the exhibition of hygromycin resistance by the transformed CC-503 strain. Insertion of the plasmid DNA including the polynucleotide into the genomic DNA was confirmed by PCR technique.

The produced algal strain with overexpression of AtMEX1 is referred to as "modified strain with suppressed expression of ATG8 (CC-503/AtMEX1ox)".

<Production of Modified Strain with Suppressed Expression of ATG8: 3>

A DNA sequence complementary to the silencing construct (SEQ ID NO: 5; hereinafter, referred to as "ATG8-amiRNA") which specifically suppresses expression of the endogenous ATG8 gene of *Chlamydomonas* was ligated to the downstream of the PSAD promoter, to prepare a plasmid.

Specific procedure was as follows: A circular DNA vector for *Chlamydomonas*, pChlamiRNA3 (Molnar A et al. (2009), Plant Journal 58: 165-174) was treated with a restriction enzyme Spe I to be cleaved (DNA fragment 5). An oligonucleotide (134 bp) consisting of the sequence set forth in SEQ ID NO: 14 was prepared by the following method. Two single-stranded oligonucleotides consisting of the sequences of SEQ ID NO: 15 and SEQ ID NO: 16, respectively, were chemically synthesized. These two oligonucleotides were mixed and heated to 100° C., and then the temperature was gradually decreased to prepare a double-stranded oligonucleotide with a 5'-terminal protruding single-stranded DNA sequence consisting of four bases (5'-CTAG) (DNA fragment 6).

The DNA fragments 5 and 6 were ligated or circularized to each other using DNA Ligase (available from TAKARA BIO INC.). The circular DNA was amplified in *Escherichia coli*, and the amplification products were extracted from *E. coli* and were purified, in accordance with a known technique.

This procedure generated the base sequence set forth in SEQ ID NO: 14 in the circular DNA molecule. In the base sequence of SEQ ID NO: 14, nucleotides 6 to 28 and nucleotides 71 to 93 form base sequences which provide specificity for silencing of ATG8 in *Chlamydomonas*. In other words, the ATG8-amiRNA was designed so that the template DNA, i.e. the base sequence set forth in SEQ ID NO: 5 including the sequence of SEQ ID NO: 14, was transcribed to RNA under regulation by the PSAD promoter in the cell.

The prepared plasmid including the polynucleotide for PSAD promoter-ATG8-amiRNA was linearized with a restriction enzyme Sca I, and the linearized plasmid was introduced in the *Chlamydomonas reinhardtii* CC-503 strain by glass beads technique (see Kindle K L (1990), Proc. Natl. Acad. Sci. USA 87: 1228-1232). The transformed strain was screened to select a strain which included the polynucleotide inserted in the genomic DNA and exhibited stable inheritance of the polynucleotide to the next generation through the cell replication. The screening was based on the exhibition of paromomycin resistance by the transformed CC-503 strain. Insertion of the plasmid DNA including the polynucleotide into the genomic DNA was confirmed by PCR technique.

The produced algal strain with suppressed expression of ATG8 is referred to as "modified strain with suppressed expression of ATG8 (CC-503/ATG8amiRNA)".

<Production of Strain with Overexpression of GSH1>

A strain with overexpression of GSH1 (referred to as 22-2) was produced in accordance with the method described in PTL5 in Example 1.

<Production of Modified Strain with Overexpression of GSH1 and Suppressed Expression of ATG8: 1>

A transformed strain was produced by introducing a polynucleotide of the cell strain 22-2 with overexpression of CrGSH1 in the genome of the polynucleotide of Hsp70A-Rbc_$_s$2 promoter-CrMEX1, as in <Production of modified strain with suppressed expression of ATG8: 1>.

The produced algal strain with suppressed expression of ATG8 is referred to as "modified strain with overexpression of GSH1 and suppressed expression of ATG8 (22-2/CrMEX1ox)".

<Production of Modified Strain with Overexpression of GSH1 and Suppressed Expression of ATG8: 2>

A transformed strain was produced by introducing a polynucleotide of the cell strain 22-2 with overexpression of CrGSH1 in the genome of the polynucleotide of Hsp70A-Rbc_S2 promoter-AtMEX1, as in <Production of modified strain with suppressed expression of ATG8: 2>.

The produced algal strain with suppressed expression of ATG8 is referred to as "modified strain with overexpression of GSH1 and suppressed expression of ATG8 (22-2/AtMEX1ox)".

<Production of Modified Strain with Overexpression of GSH1 and Suppressed Expression of ATG8: 3>

A transformed strain was produced by introducing a polynucleotide of the cell strain 22-2 with overexpression of CrGSH1 in the genome of the polynucleotide of PSAD promoter-ATG8-amiRNA, as in <Production of modified strain with suppressed expression of ATG8: 3>.

The produced algal strain with suppressed expression of ATG8 is referred to as "modified strain with overexpression of GSH1 and suppressed expression of ATG8 (22-2/ATG8-amiRNA)".

Example 2

Influences on the Expression of ATG8 in the Wild-type Strain by the Overexpression of MEX1

The modified strains with suppressed expression of ATG8 produced in Example 1 (CC-503/CrMEX1ox and CC-503/AtMEX1ox) were cultured and analyzed to determine the expression of ATG8. In detail, each strain with suppressed expression of ATG8 was cultured in a TAP medium under shaking, and the cells were collected after 72 hours. The cells were then lysed and analyzed by western blotting. The wild-type *Chlamydomonas* strain CC-503 (hereinafter, referred to as "parent strain (wild-type strain)") was used as a control.

The results are shown in FIG. 1 illustrating the expressions of the ATG8 protein in the clones produced in the Example, and indicating that the expression of ATG8 was suppressed in the cells with overexpression of MEX1 (see CC-503/CrMEX1ox clones 1, 2, 3, and 16; and CC-503/AtMEX1ox clones 1, 2, 11, 12, 15, and 18). The expression level of the ATG8 protein in each clone is shown in the table below. Each expression level is a relative value (%) to that of the parent strain (wild-type strain).

TABLE 1

| | | CC-503/CrMEX1ox | | | | | | CC-503/AtMEX1ox | | | | |
|---|---|---|---|---|---|---|---|---|---|---|---|---|
| CC-503 | 1 | 2 | 3 | 14 | 15 | 16 | 1 | 2 | 11 | 12 | 15 | 18 |
| 100% | 58% | 49% | 40% | 111% | 115% | 71% | 71% | 63% | 31% | 42% | 22% | 79% |

Example 3

Influences on the Starch Production in the Wild-type Strain by Overexpression of MEX1 and Silencing of ATG8

The modified strains with suppressed expression of ATG8 produced in Example 1 (CC-503/CrMEX1ox and CC-503/AtMEX1ox) were transferred into a nitrogen-sufficient TAP medium at a cell density of $0.5 \times 10^4$ cells/ml, and then were cultured under shaking and continuous irradiation with a light intensity of 100 $\mu E/m^2/sec$ (preliminary culture). When the cells during the preliminary culture reached the logarithmic phase, the culture was centrifuged to collect the cells. The cells were then resuspended in a nitrogen-deficient TAP medium (TAP N-free medium) at a cell density of $5.0 \times 10^6$ cells/ml (replacement of medium). Cells were collected to determine the amount of starch therein, just after the replacement of the medium and after shaking culture in the nitrogen-deficient TAP medium (TAP N-free medium) for 24 hours. The determined value is an amount of starch per culture (calculated as glucose level). The wild-type strain CC-503 was used as a control.

The strain genetically modified to provide a cell with the ATG8-targeting RNA silencing construct (ATG8-amiRNA) was transferred into a nitrogen-sufficient TAP medium at a cell density of $0.5 \times 10^4$ cells/ml, and then were cultured under shaking and continuous irradiation with a light intensity of 100 $\mu E/m^2/sec$ (preliminary culture). When the cells during the preliminary culture reached the logarithmic phase, the culture was centrifuged to collect the cells. The cells were then resuspended in a nitrogen-deficient TAP medium (TAP N-free medium) at a cell density of $5.0 \times 10^6$ cells/ml (replacement of medium). Cells were collected to determine the amount of starch therein, just after the replacement of the medium and after shaking culture in the nitrogen-deficient TAP medium (TAP N-free medium) for 24 hours. The determined value is an amount of starch per culture (calculated as glucose level). The wild-type strain CC-503 was used as a control.

Figure 2:
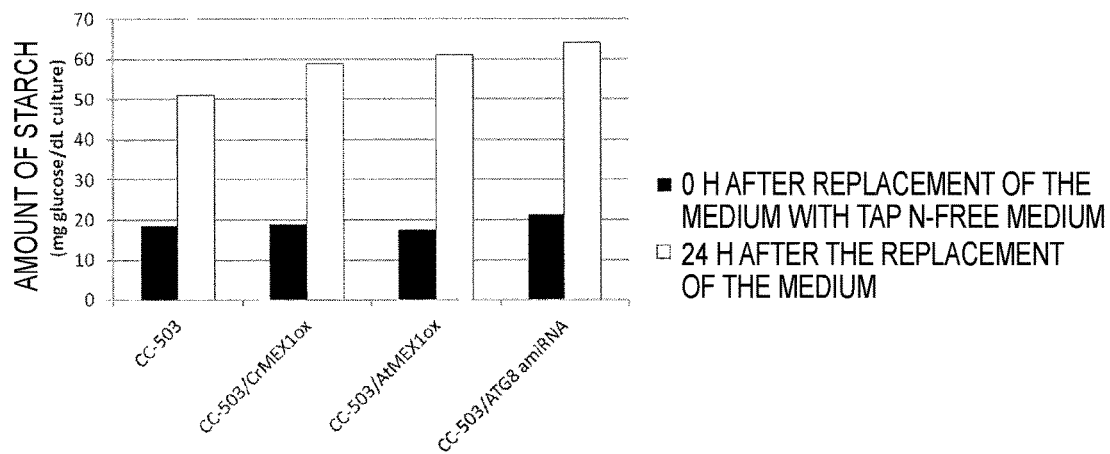
FIG. 2 illustrates the results of measurement of starch productions in the "modified strains with suppressed expression of ATG8" produced in Example 1.

The results are shown in FIG. 2 illustrating amounts of starch measured at 0 h and 24 h after the replacement of the medium with the TAP N-free medium. The results for CC-503/CrMEX1ox clone 3 and CC-503/AtMEX1ox clone 15 are shown as representative. The amount of starch was calculated as glucose level per culture (mg glucose/dL culture).

FIG. 2 demonstrates that the MEX1-overexpressing modified cells (CC-503/CrMEX1ox and CC-503/AtMEX1ox) and the ATG8-silenced modified cells (CC-503/ATG8-amiRNA) had an increased amount of starch (starch accumulation) per culture after 24 hours, as compared to that of the wild-type strain. The results indicate that the amount of starch was increased by indirect suppression of ATG8 expression through overexpression of MEX1, or direct suppression of ATG8 expression.

Example 4

Influences on ATG8 Expression in the Strain with Overexpression of GSH1 by Overexpression of MEX1

The modified strains with overexpression of GSH and suppressed expression of ATG8 produced in Example 1 (22-2/CrMEX1ox and 22-2/AtMEX1ox) were cultured and analyzed to determine the expression of ATG8. In detail, each strain with suppressed expression of ATG8 was cultured in a TAP medium under shaking, and the cells were collected after 96 hours. The cells were then lysed and analyzed by western blotting. The strain with overexpression of GSH1 (22-2) was used as a control.

Figure 3:
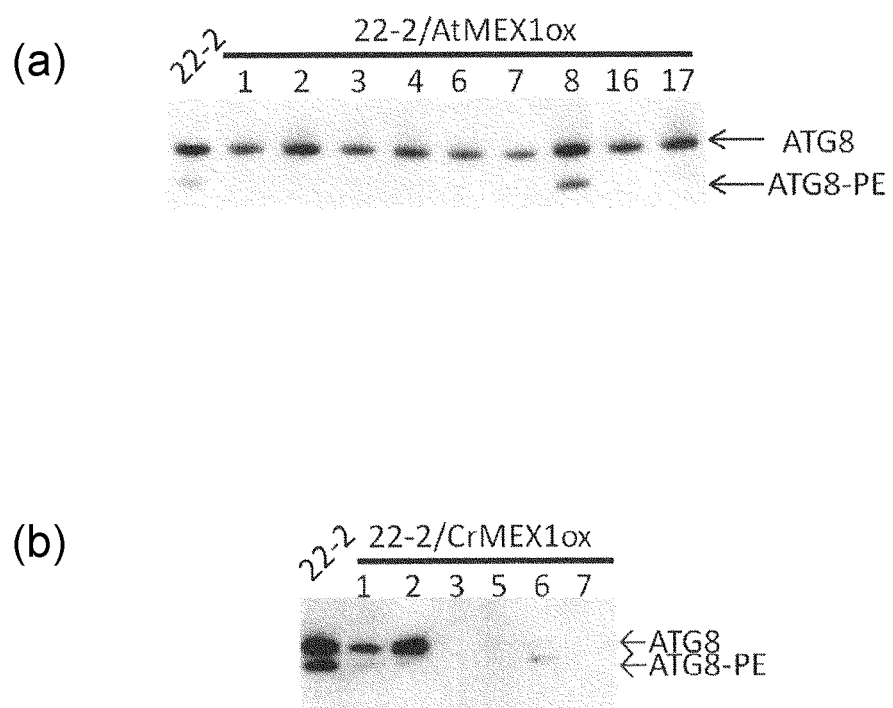
FIG. 3 illustrates the results of measurement of the ATG8 protein expressions in some of the "modified strains with overexpression of GSH1 and suppressed expression of ATG8" produced in Example 1.

The results are shown in FIG. 3. FIG. 3(a) illustrates the expressions of the ATG8 protein in clones of a strain with overexpression of GSH and suppressed expressions of ATG8 (22-2/CrMEX1ox). FIG. 3(b) illustrates the expressions of the ATG8 protein in clones of another strain with overexpression of GSH and suppressed expression of ATG8 (22-2/AtMEX1ox). The leftmost lane in each figure represents the control (22-2). The results shown in FIG. 3 indicate that the cells with overexpression of GSH1 and MEX1 exhibited suppressed expression of ATG8 and ATG-8PE (see 22-2/CrMEX1ox clones 1, 3, 5, 6, 7; and 22-2/AtMEX1ox clones 1, 2, 3, 4, 6, 7, and 16). The expressions of the ATG8 protein in the individual clones are shown in the table below. Each expression level is a relative value (%) to that of the parent strain (wild-type strain).

TABLE 2

|  | 22-2/CrMEX1ox | | | | | | | 22-2/AtMEX1ox | | | | | | | |
| --- | --- | --- | --- | --- | --- | --- | --- | --- | --- | --- | --- | --- | --- | --- | --- |
| 22-2 | 1 | 2 | 3 | 5 | 6 | 7 | 1 | 2 | 3 | 4 | 6 | 7 | 8 | 16 | 17 |
| 100% | 71% | 118% | 0 | 0 | 2% | 0 | 64% | 88% | 58% | 77% | 57% | 48% | 121% | 80% | 102% |

Example 5

Influences on Starch Production in Strains with Overexpression of GSH1 by Overexpression of MEX1

The strains with overexpression of GSH1 and suppressed expression of ATG8 produced in Example 1 (22-2/CrMEX1ox and 22-2/AtMEX1ox) were cultured and analyzed to determine the amount of starch. In detail, the cells were cultured in a TAP agar medium, and a small amount of the culture was then removed and transferred to a TAP liquid medium with a plastic inoculation loop. The cells were cultured under shaking and continuous irradiation with a light intensity of 10 $\mu E/m^2/sec$ (preliminary culture). When the cells during the preliminary culture reached the stationary phase, the culture was centrifuged to collect the cells. The cells were then diluted in a fresh TAP liquid medium at a cell density of $1.0 \times 10^4$ cells/ml, and were cultured under shaking and continuous irradiation with an intensity of light of 100 $\mu E/m^2/sec$ (main culture). The strain with overexpression of GSH1 (22-2) was used as a control.

Figure 4:
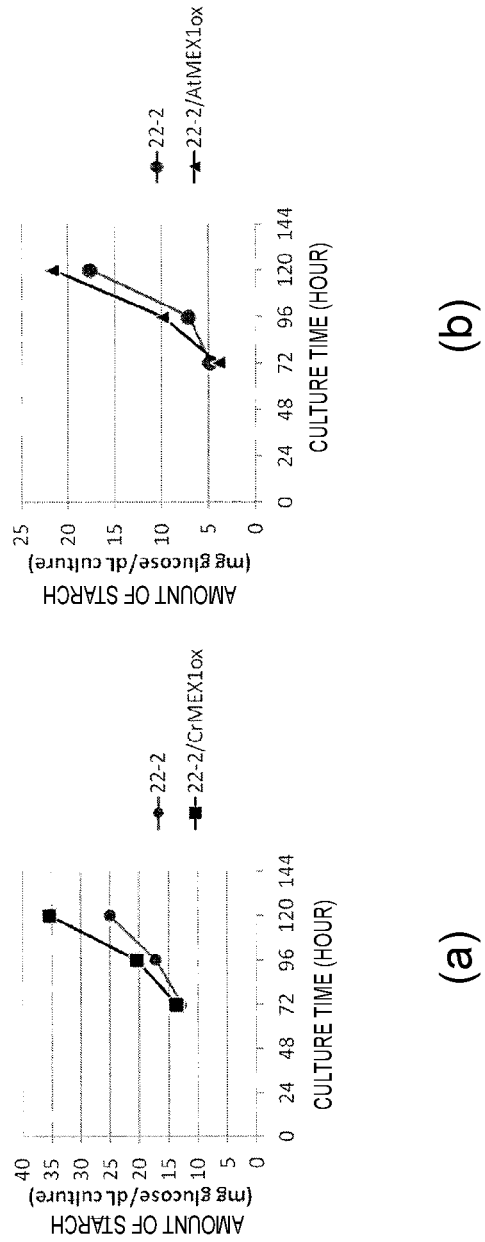
FIG. 4 illustrates the results of measurement of starch productions in some of the "modified strains with overexpression of GSH1 and suppressed expression of ATG8" produced in Example 1 and then cultured.

The results are shown in FIG. 4. FIG. 4(a) illustrates the transition of the amount of starch in the modified strain with overexpression of GSH1 and suppressed expression of ATG8 (22-2/CrMEX1ox), and FIG. 4(b) illustrates the transition of the amount of starch in another modified strain with overexpression of GSH1 and suppressed expression of ATG8 (22-2/AtMEX1ox). The results for 22-2/CrMEX1ox clone 3 and 22-2/AtMEX1ox clone 7 are shown as representative. In each figure, the vertical axis represents amounts of starch per culture calculated as glucose level (mg glucose/dL culture), and the horizontal axis represents culture time in the main culture process.

FIG. 4 demonstrates that the modified strains with overexpression of GSH1 and suppressed expression of ATG8 (22-2/CrMEX1ox and 22-2/AtMEX1ox) had an increased amount of starch per culture after 96 hours from the initiation of the main culture, as compared to that of the strain with overexpression of GSH1 (22-2). Such results indicate that the overexpression of MEX1 and the suppression of ATG8 expression increase an amount of starch.

Example 6

Influences on the Cell Proliferation in the Strain with Overexpression of GSH1 by the Overexpression of MEX1

The modified strains with overexpression of GSH1 and suppressed expression of ATG8 produced in Example 1 (22-2/CrMEX1ox clone 3 and 22-2/AtMEX1ox clone 7) were cultured and analyzed to determine the amount of starch. In detail, the cells were cultured in a TAP agar medium, and a small amount of the cells was then removed and transferred to a TAP liquid medium with a plastic inoculation loop. The cells were cultured under shaking and continuous irradiation with an intensity of light of 10 μE/m$^2$/sec (preliminary culture). When the cells during the preliminary culture reached the stationary phase, the culture was centrifuged to collect the cells. The cells were then diluted in afresh TAP liquid medium at a cell density of 1.0×10$^4$ cells/ml, and were cultured under shaking and continuous irradiation with an intensity of light of 100 μE/m$^2$/sec (main culture). The strain with overexpression of GSH1 (22-2) was used as a control.

Figure 5:
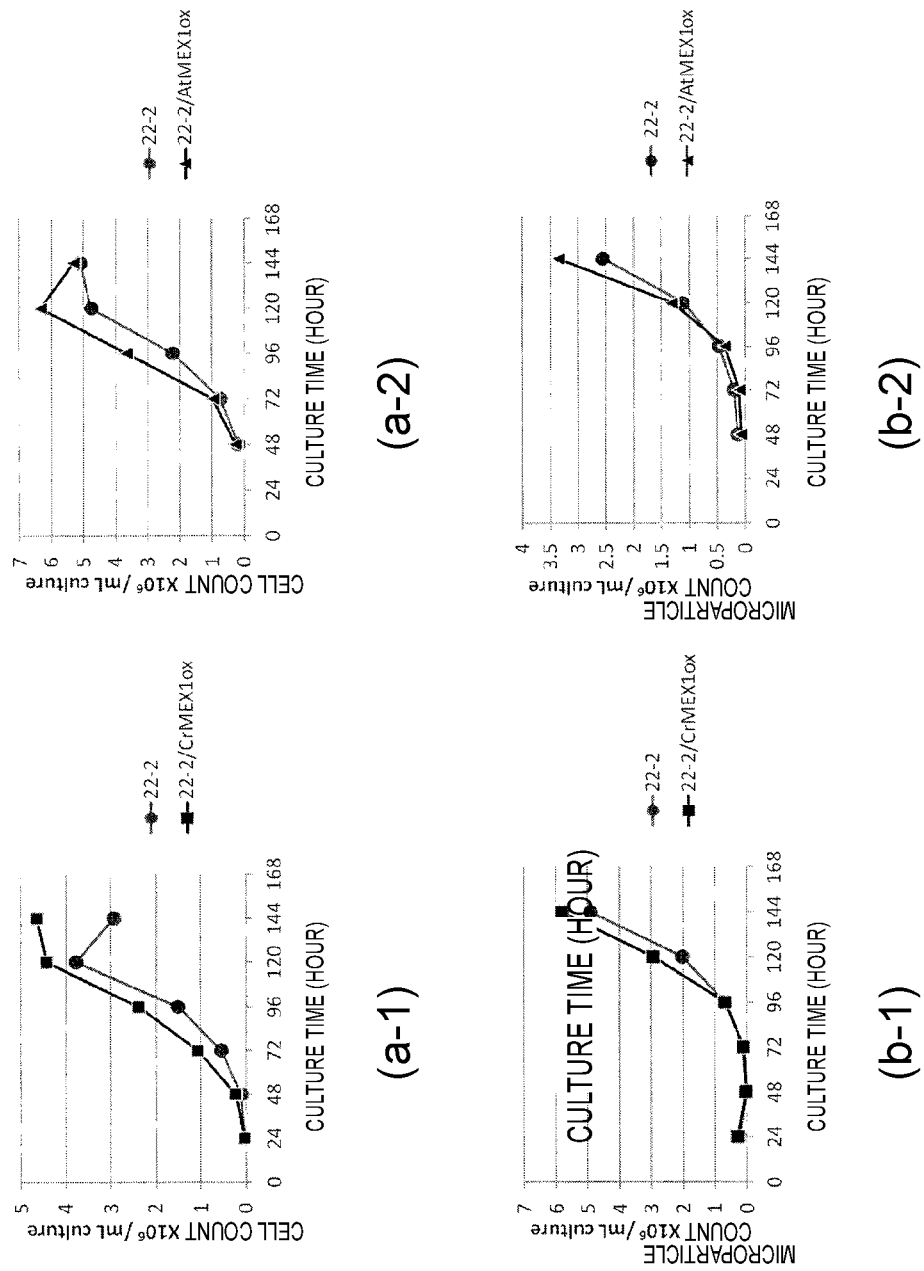
FIG. 5 illustrates the results of measurement of (a) cell counts and (b) microparticle counts in some of the "modified strains with overexpression of GSH1 and suppressed expression of ATG8" produced in Example 1 and then cultured.

The results are shown in FIG. 5. FIG. 5(a-1) illustrates the transition of the cell count of the modified strain with overexpression of GSH1 and suppressed expression of ATG8 (22-2/CrMEX1ox), and FIG. 5(a-2) illustrates the transition of the cell count of another modified strain with overexpression of GSH1 and suppressed expression of ATG8 (22-2/AtMEX1ox). FIG. 5(b-1) illustrates the transition of the microparticle count of the modified strain with overexpression of GSH1 and suppressed expression of ATG8 (22-2/CrMEX1ox), and FIG. 5(b-2) illustrates the transition of the microparticle count of another modified strain with overexpression of GSH1 and suppressed expression of ATG8 (22-2/AtMEX1ox). In the graphs shown in FIG. 5(a), the vertical axis represents the cell counts per culture (mL culture), and the horizontal axis represents the culture time in the main culture process. In the graphs FIG. 5(b), the vertical axis represents the counts of non-cellular microparticles per culture (mL culture), and the horizontal axis represents the culture time in the main culture process.

FIGS. 5(a-1) and 5(a-2) demonstrate that the cell proliferation was promoted in the modified strains with overexpression of GSH1 and suppressed expression of ATG8 (22-2/CrMEX1ox and 22-2/AtMEX1ox) as compared to the control, i.e. the strain with overexpression of GSH1 (22-2). FIGS. 5(b-1) and 5(b-2) demonstrate that the modified strains with overexpression of GSH1 and suppressed expression of ATG8 (22-2/CrMEX1ox and 22-2/AtMEX1ox) had a higher microparticle count after about 96 hours from the initiation of the culture, as compared to the strain with overexpression of GSH1 (22-2). The microparticles are presumed to be starch granules leaking from dead cells into the medium. Accordingly, the results suggest that extracellular release of starch was promoted.

Example 7

Influences on the Starch Production in the Strain with Overexpression of GSH1 by ATG8 Silencing The modified strain with overexpression of GSH1 and suppressed expression of ATG8 produced in Example 1 (22-2/ATG8amiRNA) was cultured and analyzed to observe the cell proliferation and the amount of starch. In detail, the cells were cultured in a TAP agar medium, and a small amount of the cells was then removed and transferred to a TAP liquid medium with a plastic inoculation loop. The cells were cultured under shaking and continuous irradiation with an intensity of light of 10 μE/m$^2$/sec (preliminary culture). When the cells during the preliminary culture reached the stationary phase, the culture was centrifuged to collect the cells. The cells were then diluted in a fresh TAP liquid medium at a cell density of 1.0×10$^4$ cells/ml, and were cultured under shaking and continuous irradiation with a light intensity of 100 μE/m$^2$/sec (main culture). The strain with overexpression of GSH1 (22-2) was used as a control.

Figure 6:
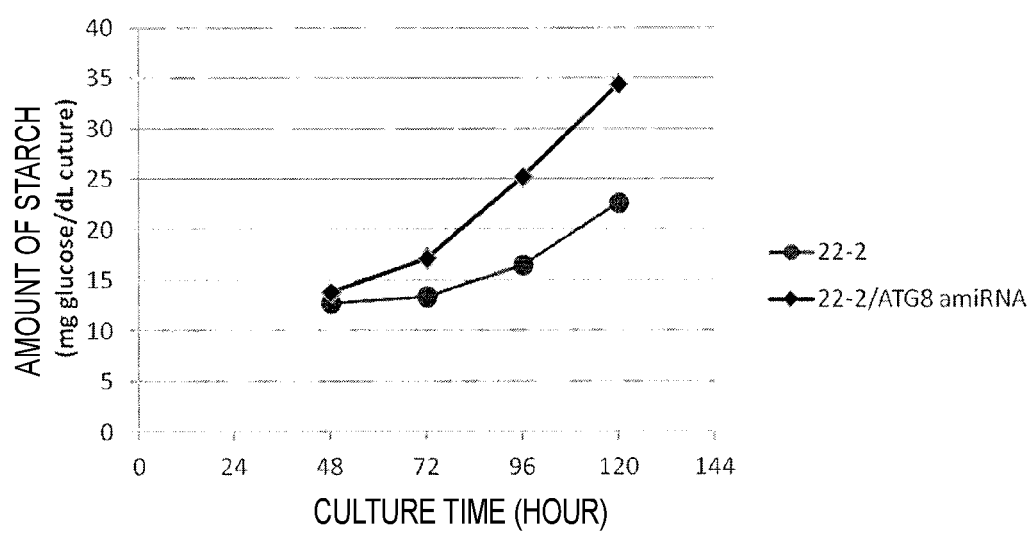
FIG. 6 illustrates the results of measurement of starch productions in one of the "modified strains with overexpression of GSH1 and suppressed expression of ATG8" produced in Example 1 and then cultured.

The results are shown in FIG. 6. FIG. 6 illustrates the transition of the amount of starch, where the vertical axis represents the amounts of starch per culture calculated as glucose level (mg glucose/dL culture) and the horizontal axis represents culture time in the main culture process.

FIG. 6 demonstrates that the modified strain with overexpression of GSH1 and suppressed expression of ATG8 (22-2/amiATG8) exhibited an increase in the amount of starch per culture after 72 hours from the initiation of the main culture, as compared to that of the strain with overexpression of GSH1 (22-2). Such results indicate that suppressing the expression of the ATG8 gene further increases the amount of accumulated starch in the strain with overexpression of GSH1.

Example 8

Influences on the Cell Proliferation in the Strain with Overexpression of GSH1 by ATG8 Silencing The modified strain with overexpression of GSH1 and suppressed expression of ATG8 produced in Example 1 (22-2/ATG8amiRNA) were cultured and analyzed to observe the cell proliferation and the amount of starch. In detail, the cells were cultured in a TAP agar medium, and a small amount of the cells was then removed and transferred to a TAP liquid medium with a plastic inoculation loop. The cells were cultured under shaking and continuous irradiation with a light intensity of 10 μE/m$^2$/sec (preliminary culture). When the cells during the preliminary culture reached almost the stationary phase, the culture was centrifuged to collect the cells. The cells were then diluted in afresh TAP liquid medium at a cell density of 1.0×10$^4$ cells/ml, and were cultured under shaking and continuous irradiation with a light intensity of 100 μE/m$^2$/sec (main culture). The strain with overexpression of GSH1 (22-2) was used as a control.

Figure 7:
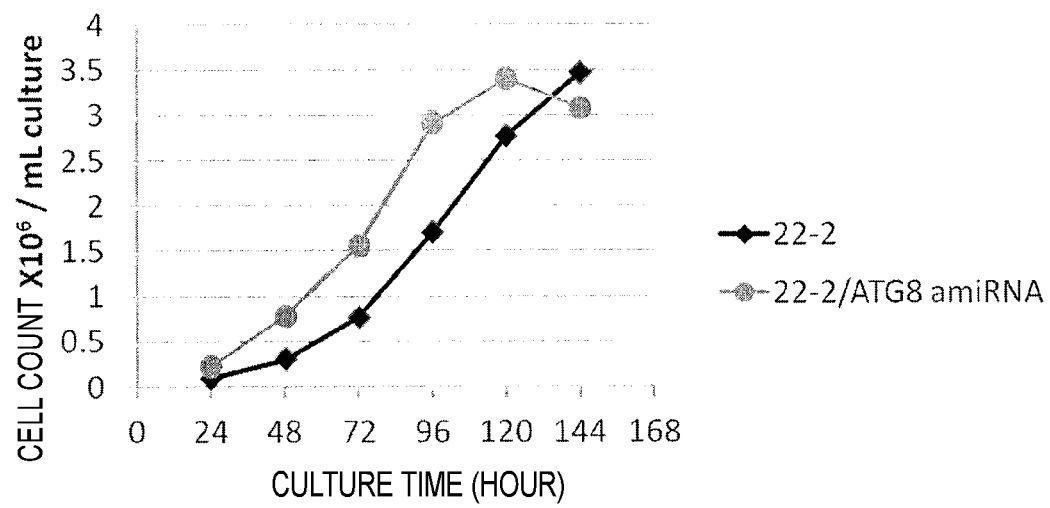
FIG. 7 illustrates the results of measurement of (a) cell counts and (b) microparticle counts in the one of the "modified strains with overexpression of GSH1 and suppressed expression of ATG8" produced in Example 1 and then cultured.
Figure 7:
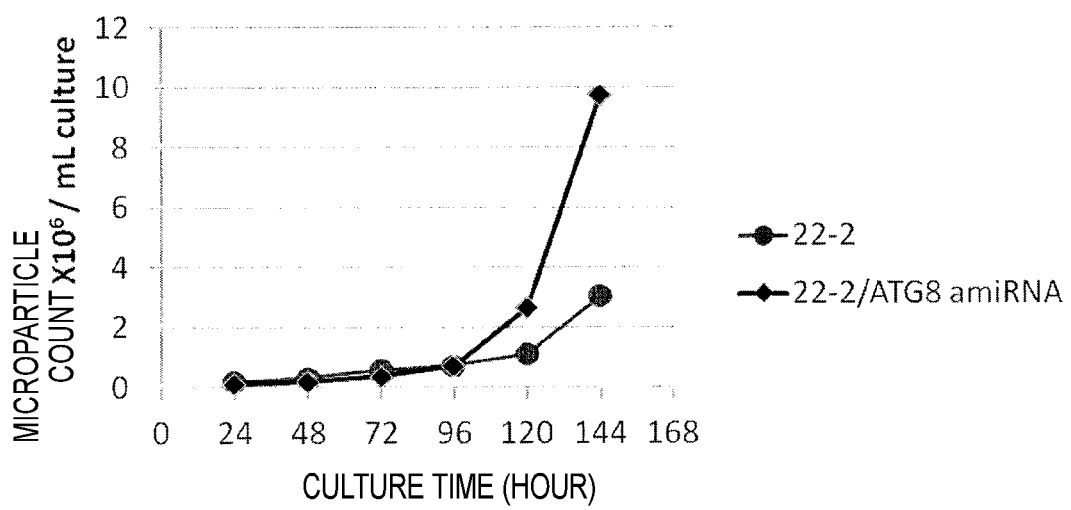

The results are shown in FIG. 7. FIG. 7(a) illustrates the transition of the cell count, and FIG. 7(b) illustrates the transition of the microparticle count. In the graph (a), the vertical axis represents the cell counts per culture (mL culture), and the horizontal axis represents the culture time in the main culture process. In the graph (b), the vertical axis represents the microparticle counts per culture (mL culture), and the horizontal axis represents the culture time in the main culture process.

FIG. 7(a) indicates that the cell proliferation was promoted in the modified strain with overexpression of GSH1 and suppressed expression of ATG8 (22-2amiATG8) as compared to that of the control strain with overexpression of GSH1 (22-2). FIG. 7(b) indicates that the modified strain with overexpression of GSH1 and suppressed expression of ATG8 (22-2amiATG8) had a higher microparticle count after 120 hours from the initiation of culture as compared to that of the strain with overexpression of GSH1 (22-2). The microparticles are presumed to be starch granules leaking from dead cells into the medium. Accordingly, the results suggest that extracellular release of starch was promoted.

Example 9

Influences on the Production of Oils and Fats in the Strain with Overexpression of GSH1 by Suppression of ATG8 Expression The modified strains with overexpression of GSH1 and suppressed expression of ATG8 (22-2/CrMEX1ox, 22-2/AtMEX1ox, and 22-2/ATG8amiRNA) produced in Example 1 were cultured and analyzed to determine the amount of oils and fats. The strain with overexpression of GSH1 (22-2) was used as a control. Each strain was cultured under the same conditions as in Example 6, except that the light intensity in the continuous irradiation in the main culture was 170 µE/m$^2$/sec. A part of each culture was daily collected in a glass tube and was cryopreserved until the analysis.

Oils and fats were collected from the cells by the following procedure. The gaseous phase of the glass tube was purged with nitrogen, and 20 µg of pentadecanoic acid was added as internal control for determination of oils and fats. A suitable amount of a methanol-hexane mixture (1:1) was added, and then the resulting mixture was stirred and left to stand. The solution was then centrifuged to be separated into aqueous and organic solvent phases. The organic solvent fraction was transferred to a different glass tube, and was dried under vacuum. The product was dissolved in a suitable amount of hexane, and was mixed with a suitable amount of 2.5% methanolic sulfuric acid solution. The gaseous phase of the glass tube was purged with nitrogen gas, and the glass tube was heated at 80° C. for one hour. After the glass tube was cooled to a room temperature, 1 ml of saturated aqueous sodium carbonate solution was added, and the mixture was stirred. The solution was then centrifuged, and the organic solvent phase was collected and dried under vacuum. The product was dissolved in 200 µL of hexane, and the solution was injected in a gas chromatograph/mass spectrometer (Clarus SQ8; available from PerkinElmer, Inc.) and was analyzed to determine fatty acid methyl esters, using a column Elite-225 available from PerkinElmer, Inc. (length: 30 m, inner diameter: 0.25 mm, film thickness: 0.25 µm). The oven was heated at 3° C./minute to 200° C. and then was maintained at 200° C. for 6.5 minutes.

Commercially available fatty acid methyl esters were used to generate a calibration curve. The sum of palmitic acid (C16:0), stearic acid (C18:0), oleic acid (C18:1), linoleic acid (C18:2), and linolenic acid (C18:3) was calculated as the amount of fatty acids. FIGS. 8(a) and 8(b) illustrate the measured amount of fatty acids and cell count, respectively. The vertical axis represents amounts of fatty acids (pg) or cell count (×10$^6$ cells) per culture (mL culture), and the horizontal axis represents the culture time (days) after the initiation of the main culture. The results for 22-2/CrMEX1ox clone 1 and 22-2/AtMEX1ox clone 7 are shown as representative.

Figure 8:
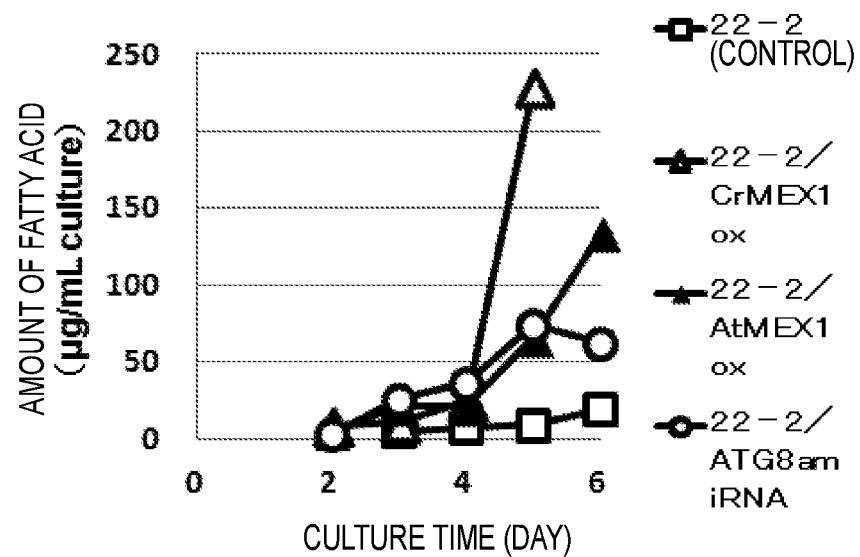
FIG. 8 illustrates the results of measurement of (a) fatty acid levels and (b) cell counts in the "modified strains with overexpression of GSH1 and suppressed expression of ATG8" produced in Example 1 and then cultured.
Figure 8:
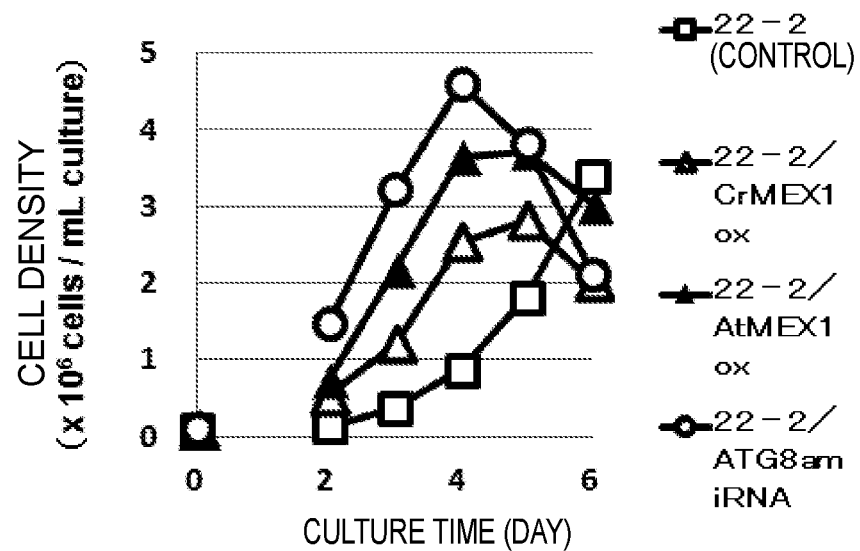

FIG. 8 demonstrates that the modified strains with overexpression of GSH1 and suppressed expression of ATG8 accumulated more fatty acids and reached to the maximum level in a shorter culture time, as compared to the strain with overexpression of GSH1 (22-2). Such results indicate that suppression of ATG8 expression increases an amount of oils and fats.

INDUSTRIAL APPLICABILITY

The present invention provides algal biomass production with lower costs and higher efficiency than traditional methods. Biomass is a promising raw material for biofuels, and therefore the invention is applicable to a wide variety of industries including the energy industry.

SEQUENCE LISTING FREE TEXT

SEQ ID NO: 1: an amino acid sequence of an MEX1 protein derived from *Arabidopsis thaliana*
SEQ ID NO: 2: a base sequence of a polynucleotide encoding the MEX1 protein derived from *Arabidopsis thaliana*
SEQ ID NO: 3: an amino acid sequence of an MEX1 protein derived from *Chlamydomonas reinhardtii*
SEQ ID NO: 4: a base sequence of a polynucleotide encoding the MEX1 protein derived from *Chlamydomonas reinhardtii*
SEQ ID NO: 5: a base sequence of ATG8-amiRNA
SEQ ID NO: 6: an amino acid sequence of γ-glutamylcysteine synthetase derived from *Chlamydomonas reinhardtii*
SEQ ID NO: 7: a base sequence of a polynucleotide encoding γ-glutamylcysteine synthetase derived from *Chlamydomonas reinhardtii*
SEQ ID NO: 8: a base sequence of a template of *Chlamydomonas reinhardtii* MEX1 cDNA
SEQ ID NO: 9: a base sequence of a primer used in amplification of the template of *Chlamydomonas reinhardtii* MEX1 cDNA
SEQ ID NO: 10: a base sequence of a primer used in amplification of the template of *Chlamydomonas reinhardtii* MEX1 cDNA
SEQ ID NO: 11: a base sequence of a template of *Arabidopsis thaliana* MEX1 cDNA
SEQ ID NO: 12: a base sequence of a primer used in amplification of a template of *Arabidopsis thaliana* MEX1 cDNA
SEQ ID NO: 13: a base sequence of a primer used in amplification of a template of *Arabidopsis thaliana* MEX1 cDNA
SEQ ID NO: 14: a base sequence of a template of ATG8-amiRNA
SEQ ID NO: 15: a base sequence of a single-stranded oligonucleotide for the synthesis of ATG8-amiRNA
SEQ ID NO: 16: a base sequence of a single-stranded oligonucleotide for the synthesis of ATG8-amiRNA
SEQ ID NO: 17: an amino acid sequence of an MEX1 protein derived from *Arabidopsis thaliana*
SEQ ID NO: 18: a base sequence of a polynucleotide encoding the MEX1 protein derived from *Arabidopsis thaliana*
SEQ ID NO: 19: an amino acid sequence of an MEX1 protein derived from *Chlamydomonas reinhardtii*
SEQ ID NO: 20: a base sequence of a polynucleotide encoding the MEX1 protein derived from *Chlamydomonas reinhardtii*

What is claimed is:

1. A method of biomass production, comprising:

irradiating with light a modified alga, thereby photoirradiating the modified alga, wherein the modified alga has suppressed intracellular expression of ATG8 as compared to that of a reference strain, wherein the reference strain is an alga otherwise identical to the modified alga but which lacks suppression of intracellular ATG8 expression, and wherein the intracellular ATG8 expression in the modified alga is 0.9 times or less as compared to that of the reference strain cultured under the same conditions; and recovering photosynthate by separating starch granules produced by the modified alga from the modified alga or a lysate thereof.

2. The method according to claim 1, wherein the modified alga has an increased chloroplastic glutathione concentration as compared to that of the reference strain.

3. The method according to claim 2, wherein the photoirradiation step is carried out on the modified alga in a culture medium having an inorganic nitrogen content of 0.001% to 0.1% by weight.

4. The method according to claim 3, wherein the method comprises no cell lysis step to disrupt algal cells.

* * * * *

SEQUENCE LISTING

<160> NUMBER OF SEQ ID NOS: 20

<210> SEQ ID NO 1
<211> LENGTH: 422
<212> TYPE: PRT
<213> ORGANISM: Arabidopsis thaliana

<400> SEQUENCE: 1

```
Met Ala Arg Arg Phe Glu Val Pro Glu Gly Lys Ala Ile Ala Thr Ser
1               5                   10                  15

Leu Gly Gly Asp Arg Val Leu Ile Phe Pro Cys Ser Pro Arg Ser Ser
            20                  25                  30

Phe Val Phe Thr Ser Arg Leu Ser Ser Leu Pro Leu Lys Arg Ala Ser
                35                  40                  45

Ile Gly Gly Ala Val Ser Cys Ser Gly Val Asn Gly Leu Thr Arg Trp
50                  55                  60

Asn Ser Ile Val Ser Thr Arg Arg Leu Val Pro Val Arg Ser Ile Asn
65                  70                  75                  80

Ser Glu Ser Asp Ser Asp Ser Asp Phe Pro His Glu Asn Gln Gln Gly
                85                  90                  95

Asn Pro Gly Leu Gly Lys Phe Lys Glu Tyr Gln Glu Trp Asp Ser Trp
            100                 105                 110

Thr Ala Lys Phe Ser Gly Gly Ala Asn Ile Pro Phe Leu Met Leu Gln
                115                 120                 125

Leu Pro Gln Ile Ile Leu Asn Thr Gln Asn Leu Leu Ala Gly Asn Asn
            130                 135                 140

Thr Ala Leu Ser Ala Val Pro Trp Leu Gly Met Leu Thr Gly Leu Leu
145                 150                 155                 160

Gly Asn Leu Ser Leu Leu Ser Tyr Phe Ala Lys Lys Arg Glu Lys Glu
                165                 170                 175

Ala Ala Val Val Gln Thr Leu Gly Val Val Ser Thr His Ile Val Leu
            180                 185                 190

Ala Gln Leu Thr Met Ala Glu Ala Met Pro Ile Gln Tyr Phe Val Ala
        195                 200                 205

Thr Ser Ala Val Val Thr Ile Gly Leu Ile Val Asn Cys Leu Tyr Tyr
210                 215                 220

Phe Gly Lys Leu Ser Lys Thr Val Trp Gln Leu Trp Glu Asp Val Ile
225                 230                 235                 240

Thr Ile Gly Gly Leu Ser Val Leu Pro Gln Ile Met Trp Ser Thr Phe
                245                 250                 255

Val Pro Leu Val Pro Asn Ser Ile Leu Pro Gly Thr Thr Ala Phe Gly
            260                 265                 270

Ile Ala Val Ala Ala Ile Ile Met Ala Arg Thr Gly Lys Leu Ser Glu
        275                 280                 285

Lys Gly Val Arg Phe Val Gly Ser Leu Ser Gly Trp Thr Ala Thr Leu
            290                 295                 300

Met Phe Met Trp Met Pro Val Ser Gln Met Trp Thr Asn Phe Leu Asn
305                 310                 315                 320

Pro Asp Asn Ile Lys Gly Leu Ser Ser Ile Thr Met Leu Leu Ser Met
                325                 330                 335

Met Gly Asn Gly Leu Met Ile Pro Arg Ala Leu Phe Ile Arg Asp Leu
            340                 345                 350

Met Trp Leu Thr Gly Ser Leu Trp Ala Thr Leu Phe Tyr Gly Tyr Gly
        355                 360                 365
```

```
Asn Ile Leu Cys Leu Tyr Leu Val Asn Cys Thr Ser Gln Ser Phe Phe
    370             375                 380

Val Ala Ala Thr Ile Gly Leu Ile Ser Trp Ile Gly Leu Ala Leu Trp
385                 390                 395                 400

Arg Asp Ala Val Ala Tyr Gly His Asn Ser Pro Phe Arg Ser Leu Lys
                405                 410                 415

Glu Leu Val Phe Gly Pro
                420

<210> SEQ ID NO 2
<211> LENGTH: 1269
<212> TYPE: DNA
<213> ORGANISM: Arabidopsis thaliana

<400> SEQUENCE: 2
atggccagga gattcgaggt accggaaggt aaagccatcg cgacgtctct cggtggtgat      60
cgtgtattga tattcccgtg ttctcctcgc tcttccttcg tttttacatc ccggctctct     120
agcctgcctc taaagcgtgc gtctatcggt ggtgctgtct cttgttccgg cgtcaatggc     180
ttgactcggt ggaattccat tgtttcgact cgccgactcg ttcctgttcg ttcaattaac     240
tcggaatcgg actcggactc cgacttccct cacgagaatc agcagggaaa tccaggtttg     300
gggaaattta ggaataccaa agaatgggac tcatggacgg ccaagttctc cggtggagca     360
aacattccgt ttctcatgct ccaattgcct cagatcatcc tcaataccca gaatcttttg     420
gcgggaaaca taccgctctt tcggctgtcc catggctggg aatgttgact ggtttgtta      480 ggaaaccttt cgttgctttc ttattttgct aagaagagag aaaaagaagc agctgtggtg     540
caaacactgg gagtggtctc tactcacatt gtgcttgcac agctcacaat ggctgaagca     600
atgcctattc agtattttgt tgctacttca gctgttgtca ccatcggtct cattgtgaac     660
tgtttgtact atttcggtaa gcttagcaaa actgtgtggc aactgtggga agacgttatc     720
actattggtg gactctccgt tcttcctcaa atcatgtggt caacatttgt ccctcttgta     780
ccaaacagta tcttgcctgg acaactgct tttggtattg ctgtggcagc ataatcatg      840 gctcgaactg ggaaactttc agagaaaggt gttaggtttg tagggtcttt atctggatgg     900
acagcaactc ttatgttcat gtggatgcca gtttcccaaa tgtggacaaa ttttctaaac     960
ccggacaaca taaaaggctt atcgtcaatc acaatgttgc tctcgatgat gggaaacggg    1020
cttatgatcc ctcgagcact atttatccgt gatttgatgt ggctcactgg ttcgctatgg    1080
gcaactctct tttatggata tggaaatatt ctttgcttat acctggtaaa ttgcaccagc    1140
cagtcattct tcgtggcagc tacaattggt ttgatctcat ggataggact ggctttgtgg    1200
agagatgcag tggcttatgg tcacaactcg ccgtttagat cttgaaaga acttgttttt    1260 ggaccgtaa                                                            1269

<210> SEQ ID NO 3
<211> LENGTH: 380
<212> TYPE: PRT
<213> ORGANISM: Chlamydomonas reinhardtii

<400> SEQUENCE: 3

Met Ala Arg Arg Phe Glu Val Pro Arg Ser Leu Gln Pro Ala Pro Ala
1               5                   10                  15

Arg Ser Phe Ser Gly Met Glu Gly Arg Arg Thr Thr Gly Thr Arg Thr
                20                  25                  30

Leu Val Thr Val Ser Ser Arg Lys Lys Pro Val Pro Pro Leu His Ala
```

```
            35                  40                  45
Gly Ala Thr Ser Gly Pro Ala Ser Asp Ser Gln Arg Trp Asn Ala Leu
     50                  55                  60

Thr Asp Lys Leu Val Ala Ala Ser Ser Ile Pro Phe Ser Ile Leu Val
 65                  70                  75                  80

Leu Pro Gln Val Val Gln Asn Ala Ile Asn Met Ala Gly Gly His Pro
                 85                  90                  95

Thr Ala Leu Ser Ile Ile Ser Trp Glu Gly Tyr Leu Ser Ala Met Phe
            100                 105                 110

Gly Asn Thr Leu Met Cys Ser His Phe Ala Ala Ser Gly Glu Arg Ser
        115                 120                 125

Ala Val Asn Val Gln Leu Val Gly Ile Leu Asn Asn Phe Leu Ile Leu
    130                 135                 140

Thr Gln Val Ala Leu Ala Gly Phe Met Pro Leu Ala Val Phe Leu Ala
145                 150                 155                 160

Ala Ala Ala Phe Thr Ala Phe Ala Thr Phe Met Asn Leu Ala Arg Val
                165                 170                 175

Ala Ala Leu Ala Gly Ala Ala Gln Pro Ala Asp Glu Lys Trp Gly Ser
            180                 185                 190

Trp Gln Met Trp Gln Leu Gly Ser Gly Leu Val Gly Leu Ala Val Val
        195                 200                 205

Pro Gln Val Leu Tyr Asn Thr Val Ser Pro Ala Ala Ser Thr Leu Leu
    210                 215                 220

Pro Phe Ile Cys Thr Leu Gly Leu Leu Gly Ala Val Leu Gly Leu Arg
225                 230                 235                 240

Leu Ser Ser Lys Gly Gly Ser Asp Ala Ala Thr Leu Val Arg Gln Leu
                245                 250                 255

Pro Gly Trp Gly Ala Thr Leu Leu Phe Ala Leu Ser Pro Leu Pro Gln
            260                 265                 270

Leu Val Arg Asn Leu Leu Glu Pro Gln Ser Leu Glu Gly Leu Ser Val
        275                 280                 285

Gly Thr Met Leu Leu Ala Leu Leu Gly Asn Ala Leu Met Val Pro Arg
    290                 295                 300

Ala Leu Phe Val Arg Asp Val Val Trp Leu Ser Gly Thr Cys Trp Ala
305                 310                 315                 320

Cys Val Ala Gly Trp Gly Gln Leu Phe Ser Met Phe Arg Ser Ala Ser
                325                 330                 335

Ala Ala Thr Gly Arg Arg Phe Leu Asp Pro Trp Leu Phe Phe Ser Ile
            340                 345                 350

Thr Gly Ala Leu Leu Leu Tyr Thr Gly Tyr Val Val Val Gln His Arg
        355                 360                 365

Arg Ala Thr Ala Ala Ala Ser Pro Arg Pro Ala
    370                 375                 380

<210> SEQ ID NO 4
<211> LENGTH: 1143
<212> TYPE: DNA
<213> ORGANISM: Chlamydomonas reinhardtii

<400> SEQUENCE: 4
atggccagga gattcgaggt accgagatct ttgcaaccgg caccggcaag gagtttttcg      60
gggatggaag ggcgacggac aacaggcacg cgaacgctgg tgactgtcag tagccggaaa     120
aagcccgtgc ccccgttgca tgcgggagca acgagcggtc cggcaagcga cagccagcga     180
```

```
tggaatgcgc tcacggacaa gctggtggct gcatccagca ttccgttctc tatttttggtg    240 cttccgcaag tcgtccagaa tgccatcaac atggctggcg ccacccccac ggccctgtcc    300
attatcagct gggagggcta cctctctgcc atgttcggca acacattaat gtgcagccat    360
ttcgcggcgt caggcgagcg cagcgccgta acgtgcagc ttgtgggaat cctcaacaac     420
ttcctcattc tcacacaggt ggctcttgcc ggcttcatgc cgctcgcggt gttttttggcg   480 gcggcggcct tcacggcctt tgccactttt atgaacctgg cacgcgtggc ggcgctggcg    540
ggcgcagcgc agccggcgga cgagaagtgg ggcagctggc agatgtggca gctgggcagc    600
gggctggtgg ggctggcggt ggtgccgcag gtgctctaca acaccgtgtc cccggcggca    660
tccacgctgc tgcccttcat ttgcacgctt gggctgcttg gagcggtgct agggctacgg    720
ctgtcgtcca agggcggtag cgacgcggca acgctggtgc ggcagctgcc gggctggggc    780
gccacgctgc tgtttgcgct gtcgccgcta ccgcagctgg tccgcaacct gcttgagcca    840
cagagcctgg agggcctgag cgtgggcacc atgctgctgg cgctgctggg caacgcgctc    900
atggtgccgc gggcgctgtt cgtgcgcgac gtggtgtggt cagcggcac ctgctgggcc     960 tgcgtagcgg gctggggtca gctgttcagc atgttccgca gcgcgtcggc ggccacaggg    1020
cggcgcttcc tggaccctg gctgttcttc tccatcaccg gggcgctgct gctgtacact     1080
ggctacgtgg tggtgcagca ccggagagcc acagcggcgg cagcaagccc gcggcccgca    1140
taa                                                                 1143

<210> SEQ ID NO 5
<211> LENGTH: 212
<212> TYPE: RNA
<213> ORGANISM: Artificial Sequence
<220> FEATURE:
<223> OTHER INFORMATION: ATG8 miRNA nucleic acid sequence

<400> SEQUENCE: 5
acaugcccag gaaaccaagg cgcgcuagcu uccugggcgc aguguuccag cuacuagaga     60
aggcaccagg uacuucaucu uucucgcuga ucggcaccau gggggugugug gugaucagcg    120 cuaaagaaga aguaccuggu gccuucgcua guagccggaa cacugccagg aaggaggggg    180
aggcugggug ggagaagcgg uguggggcgg au                                  212

<210> SEQ ID NO 6
<211> LENGTH: 479
<212> TYPE: PRT
<213> ORGANISM: Chlamydomonas reinhardtii

<400> SEQUENCE: 6

Met Ala Leu Ala Ser Gly Val Gly Arg Arg Gln His Val Ser Ala Ser
1               5                   10                  15

Pro Ser Arg Ser Arg Gly Val Pro Ser Pro Arg Leu Ser Pro Val His
                20                  25                  30

Ala Asn Ala Pro Ala Val Ala Glu Arg Arg Thr Glu Pro Leu Leu Lys
            35                  40                  45

Gln Glu Leu Val Asp Tyr Leu Lys Ser Gly Cys Arg Pro Arg Ser Ala
        50                  55                  60

Trp Arg Ile Gly Thr Glu His Glu Lys Leu Gly Phe Asn Leu Ala Asp
65                  70                  75                  80

Asn Ser Arg Met Asn Tyr Asp Gln Ile Ala Gln Val Leu Arg Lys Leu
                85                  90                  95

Glu Ala Arg Phe Gly Trp Glu Pro Ile Met Glu Glu Gly Arg Ile Ile
```

```
            100                 105                 110
Gly Val Gln Leu Asp Gly Gln Ser Val Thr Leu Glu Pro Gly Gly Gln
            115                 120                 125
Phe Glu Leu Ser Gly Ala Pro Val Glu Thr Ile His Lys Thr Cys Ala
            130                 135             140
Glu Val Asn Ser His Leu Tyr Gln Val Lys Ala Ile Cys Glu Glu Leu
145                 150                 155                 160
Gln Thr Gly Phe Leu Gly Val Gly Phe Asp Pro Lys Trp Ala Ile Ser
                165                 170                 175
Asp Val Pro Met Met Pro Lys Gly Arg Tyr Lys Leu Met Lys Ser Tyr
            180                 185                 190
Met Pro Thr Val Gly Ser Met Gly Leu Asp Met Met Phe Arg Thr Cys
            195                 200                 205
Thr Val Gln Val Asn Leu Asp Phe Glu Ser Glu Gln Asp Met Val Glu
            210                 215                 220
Lys Phe Arg Ile Gly Leu Ala Leu Gln Pro Ile Ala Asn Ala Leu Phe
225                 230                 235                 240
Ala Ser Ser Pro Phe Lys Glu Gly Lys Pro Thr Gly Tyr Leu Ser Thr
                245                 250                 255
Arg Gly His Val Trp Thr Asp Val Asp Ala Ser Arg Thr Gly Asn Leu
            260                 265                 270
Pro Phe Val Phe Glu Lys Asp Met Cys Phe Glu Ser Tyr Val Asp Tyr
            275                 280                 285
Ala Met Ala Val Pro Met Tyr Phe Val Tyr Arg Asn Gly Gln Tyr Ile
            290                 295                 300
Asn Ala Leu Gly Met Ser Trp Lys Asp Phe Met Ala Gly Lys Leu Pro
305                 310                 315                 320
Ala Leu Pro Gly Glu Tyr Pro Thr Ile Ala Asp Trp Ala Asn His Leu
                325                 330                 335
Thr Thr Ile Phe Pro Glu Val Arg Leu Lys Lys Phe Leu Glu Met Arg
            340                 345                 350
Gly Ala Asp Gly Gly Pro Trp Arg Met Leu Cys Ala Leu Pro Ala Leu
            355                 360                 365
Trp Val Gly Leu Ile Tyr Asp Pro Glu Ala Gln Arg Gln Ala Leu Ala
            370                 375                 380
Leu Ile Glu Asp Trp Thr Pro Ala Glu Arg Asp Tyr Leu Arg Thr Glu
385                 390                 395                 400
Val Thr Arg Phe Gly Leu Arg Thr Pro Phe Arg Ala Gly Thr Val Gln
                405                 410                 415
Asp Val Ala Lys Gln Val Val Ser Ile Ala His Gly Gly Leu Glu Arg
            420                 425                 430
Arg Gly Tyr Asp Glu Thr Ser Phe Leu Lys Arg Leu Glu Val Ile Ala
            435                 440                 445
Glu Thr Gly Leu Thr Gln Ala Asp His Leu Leu Glu Leu Tyr Glu Thr
            450                 455                 460
Lys Trp Gln Arg Ser Val Asp Pro Leu Tyr Lys Glu Phe Met Tyr
465                 470                 475

<210> SEQ ID NO 7
<211> LENGTH: 1440
<212> TYPE: DNA
<213> ORGANISM: Chlamydomonas reinhardtii

<400> SEQUENCE: 7
```

| atggctctcg cctcaggcgt tggccgtcgc cagcatgtgt cggcctcgcc ctcgcgcagt | 60 |
| cggggtgtgc caagcccacg cttgagccct gtccacgcga acgcgcctgc ggttgcggag | 120 |
| cgtcgcacag agcccctctt aaagcaggag ctggtggatt acctgaaatc ggggtgtagg | 180 |
| cctcgcagcg cgtggcgaat cggcaccgag acgagaagc tgggtttcaa cctggcagac | 240 |
| aacagccgca tgaactacga ccagattgca caggtgctac gcaagctgga ggcccggttt | 300 |
| ggttgggagc ccatcatgga ggagggccgt atcatcggcg tgcagttgga tggtcagagt | 360 |
| gtgacgctgg agcccggcgg ccagtttgaa ctgagcgggg cgccgtgga gaccattcac | 420 |
| aagacgtgtg cggaggtgaa cagccacctc taccaggtca aggccatctg cgaggagctt | 480 |
| cagacaggat tcctgggcgt gggctttgac cccaagtggg ccatcagcga cgttcccatg | 540 |
| atgcccaagg ccgctacaa gctgatgaag tcgtacatgc ccacggtggg ctccatgggc | 600 |
| ctggacatga tgttccgcac atgcaccgtg caggtgaacc tggactttga gagcgagcag | 660 |
| gacatggtgg agaagttccg catcggcctg cgctgcagc ccatcgccaa cgcgctcttc | 720 |
| gccagctcgc cattcaagga gggcaagccc accgggtacc tgagcaccc cggtcacgtg | 780 |
| tggacgacg tggacgcctc gcgcaccggc aacctgccgt tcgtgttcga aaggacatg | 840 |
| tgcttcgaga gctacgtgga ctacgccatg gcggtgccca tgtacttcgt gtaccgcaac | 900 |
| gggcagtaca tcaacgcgct gggcatgagc tggaaggact tcatggccgg caagctgccc | 960 |
| gcgctgccgg cgaatacccc accatcgcc gactgggcca accacctgac caccatcttc | 1020 |
| cccgaggtgc ggctcaagaa gttcctggag atgcgcggcg cggacggcgg ccctggcgc | 1080 |
| atgctgtgcg cgctgccggc gctgtgggtg ggctcatat cgatccgga ggcgcagcgc | 1140 |
| caggccctgg cgctgattga ggattggacg cccgcggagc gcgactacct gcgcaccgag | 1200 |
| gtgacccgct tcggcctgcg cacgcccttc gcgccggca ccgtgcagga cgtgccaag | 1260 |
| caggtggtgt ccatcgcgca cggcggcctg gagcggcgag gctacgacga acgtccttc | 1320 |
| ctcaagcgcc tggaggtcat cgcggagact ggcctcacac aggccgacca cctgcttgag | 1380 |
| ctgtacgaga ccaagtggca cgctcggtg gacccgctgt acaaggagtt catgtactga | 1440 |

<210> SEQ ID NO 8
<211> LENGTH: 1830
<212> TYPE: DNA
<213> ORGANISM: Chlamydomonas reinhardtii

<400> SEQUENCE: 8

| atggccaggt gagtcgacga gcaagcccgg cggatcaggc agcgtgcttg cagatttgac | 60 |
| ttgcaacgcc cgcattgtgt cgacgaaggc ttttggctcc tctgtcgctg tctcaagcag | 120 |
| catctaaccc tgcgtcgccg tttccatttg caggagattc gaggtaccga gatctttgca | 180 |
| accggcaccg gcaaggagtt tttcggggat ggaagggcga cggacaacag gcacgcgaac | 240 |
| gctggtgact gtcagtagcc ggaaaaagcc cgtgcccccg ttgcatgcgg gagcaacgag | 300 |
| cggtccggca agcgacagcc agcgatggaa tgcgctcacg acaagctgg tggctgcatc | 360 |
| cagcattccg ttctctattt tggtgcttcc gcaagtcgtc cagaatgcca tcaacatggc | 420 |
| tggcggccac cccacggccc tgtccattat cagctgggag ggtacctct gccatgtt | 480 |
| cggcaacaca ttaatgtgca gccatttcgc ggcgtcaggc gagcgcagcg ccgtaaacgt | 540 |
| gcagcttgtg gaatcctca caacttcct cattctcaca caggtggctc ttgccggctt | 600 |
| catgccgctc gcgtgttt tggcggcggc ggccttcacg gcctttgcca cttttatgaa | 660 |
| cctggcacgc gtggcggcgc tggcgggcgc agcgcagccg gcggacgaga agtggggcag | 720 |

-continued

```
ctggcagatg tggcagctgg gcagcgggct ggtggggctg gcggtggtgc cgcaggtgct    780
ctacaacacc gtgtccccgg cggcatccac gctgctgccc ttcatttgca cgcttgggct    840
gcttggagcg gtgctagggc tacggctgtc gtccaagggc ggtagcgacg cggcaacgct    900
ggtgcggcag ctgccgggct ggggcgccac gctgctgttt cgctgtcgc cgctaccgca    960 gctggtccgc aacctgcttg agccacagag cctggagggc ctgagcgtgg caccatgct    1020 gctggcgctg ctgggcaacg cgctcatggt gccgcgggcg ctgttcgtgc cgacgtggt    1080 gtggctcagc ggcacctgct gggcctgcgt agcgggctgg ggtcagctgt tcagcatgtt    1140
ccgcagcgcg tcgcggcca cagggcggcg cttcctggac ccctggctgt tcttctccat    1200
caccggggcg ctgctgctgt acactggcta cgtggtggtg cagcaccgga gagccacagc    1260
ggcggcagca agcccgcggc ccgcataaac agctgctgct cgtgatgctt aggtggacca    1320
tgttcgggac cgctggcgga gcttggcgtg gcttttgttg tgcggcgtgg ctgcaacgct    1380
ttgtcgttga acggcacatg cggtctgcgg attgcgtcgg cgggtagggc gcggagggaa    1440
ggtggtcggg tagaggctga ttccgcggtt ggatgaaggg accagtcggc ggaatcaggg    1500
cggcgcgcct gcatccaggc aagtgcaggc cggcagccag catatattca tgacatgtcg    1560
tactgctata atgtgctaga ttcaaagcca gcagctgact tggttgcaac cggcggtatt    1620
gctggtatcg tgcataaggc tcggaggcag gctactgcgc atgacactgc ctactgatac    1680
acagatagcg catggcttgc atgctatgaa aagggccagt ctgccactgc aggtacaatc    1740
gggctgtagg cggcgtaagt gagctcgggg gtgatggtgc gcaggcacat acctgcaaac    1800
aaacgacacc acagtaacaa gtgcggccgc                                    1830
```

<210> SEQ ID NO 9
<211> LENGTH: 47
<212> TYPE: DNA
<213> ORGANISM: Artificial Sequence
<220> FEATURE:
<223> OTHER INFORMATION: primer

<400> SEQUENCE: 9

```
ttttggtacc gagatctttg caaccggcac cggcaaggag ttttttcg                 47
```

<210> SEQ ID NO 10
<211> LENGTH: 43
<212> TYPE: DNA
<213> ORGANISM: Artificial Sequence
<220> FEATURE:
<223> OTHER INFORMATION: primer

<400> SEQUENCE: 10

```
ttttgcggcc gcacttgtta ctgtggtgtc gtttgtttgc agg                      43
```

<210> SEQ ID NO 11
<211> LENGTH: 1442
<212> TYPE: DNA
<213> ORGANISM: Arabidopsis thaliana

<400> SEQUENCE: 11

```
atggccaggt gagtcgacga gcaagcccgg cggatcaggc agcgtgcttg cagatttgac     60
ttgcaacgcc cgcattgtgt cgacgaaggc ttttggctcc tctgtcgctg tctcaagcag    120
catctaaccc tgcgtcgccg tttccatttg caggagattc gaggtaccgg aaggtaaagc    180
catcgcgacg tctctcggtg gtgatcgtgt attgatattc ccgtgttctc ctcgctcttc    240
```

```
cttcgttttt acatcccggc tctctagcct gcctctaaag cgtgcgtcta tcggtggtgc    300
tgtctcttgt tccggcgtca atggcttgac tcggtggaat tccattgttt cgactcgccg    360
actcgttcct gttcgttcaa ttaactcgga atcggactcg gactccgact tccctcacga    420
gaatcagcag ggaaatccag gtttggggaa atttaaggaa taccaagaat gggactcatg    480
gacggccaag ttctccggtg gagcaaacat tccgtttctc atgctccaat tgcctcagat    540
catcctcaat acccagaatc ttttggcggg aaacaatacc gctctttcgg ctgtcccatg    600
gctgggaatg ttgactggtt tgttaggaaa cctttcgttg ctttcttatt ttgctaagaa    660
gagagaaaaa gaagcagctg tggtgcaaac actgggagtg gtctctactc acattgtgct    720
tgcacagctc acaatggctg aagcaatgcc tattcagtat tttgttgcta cttcagctgt    780
tgtcaccatc ggtctcattg tgaactgttt gtactatttc ggtaagctta gcaaaactgt    840
gtggcaactg tgggaagacg ttatcactat tggtggactc tccgttcttc ctcaaatcat    900
gtggtcaaca tttgtccctc ttgtaccaaa cagtatcttg cctgggacaa ctgcttttgg    960
tattgctgtg gcagctataa tcatggctcg aactgggaaa ctttcagaga aaggtgttag   1020
gtttgtaggg tctttatctg gatggacagc aactcttatg ttcatgtgga tgccagtttc   1080
ccaaatgtgg acaaattttc taaacccgga caacataaaa ggcttatcgt caatcacaat   1140
gttgctctcg atgatgggaa cgggcttat gatccctcga gcactattta tccgtgattt   1200
gatgtggctc actggttcgc tatgggcaac tctcttttat ggatatgaa atattctttg   1260 cttatacctg gtaaattgca ccagccagtc attcttcgtg gcagctacaa ttggtttgat   1320
ctcatggata ggactggctt tgtggagaga tgcagtggct tatggtcaca actcgccgtt   1380
tagatctttg aaagaacttg tttttggacc gtaatgaatg aatgtacacg ccatgcggcc   1440
gc                                                                  1442

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
cgaggtaccg gaaggtaaag ccatcgcgac gtctc                               35

<210> SEQ ID NO 13
<211> LENGTH: 40
<212> TYPE: DNA
<213> ORGANISM: Artificial Sequence
<220> FEATURE:
<223> OTHER INFORMATION: primer

<400> SEQUENCE: 13
atggcggccg catggcgtgt acattcattc attacggtcc                          40

<210> SEQ ID NO 14
<211> LENGTH: 98
<212> TYPE: DNA
<213> ORGANISM: Artificial Sequence
<220> FEATURE:
<223> OTHER INFORMATION: Template for ATG8-amiRNA

<400> SEQUENCE: 14
ctagagaagg caccaggtac ttcatctttc tcgctgatcg gcaccatggg ggtggtggtg    60
atcagcgcta aagaagaagt acctggtgcc ttcgctag                            98
```

<210> SEQ ID NO 15
<211> LENGTH: 94
<212> TYPE: DNA
<213> ORGANISM: Artificial Sequence
<220> FEATURE:
<223> OTHER INFORMATION: Nucleic acid sequence of a single chain
      constituting template for ATG8-amiRNA

<400> SEQUENCE: 15

```
ctagagaagg caccaggtac ttcatctttc tcgctgatcg gcaccatggg ggtggtggtg      60
atcagcgcta aagaagaagt acctggtgcc ttcg                                  94
```

<210> SEQ ID NO 16
<211> LENGTH: 94
<212> TYPE: DNA
<213> ORGANISM: Artificial Sequence
<220> FEATURE:
<223> OTHER INFORMATION: Nucleic acid sequence of a single chain
      constituting template for ATG8-amiRNA

<400> SEQUENCE: 16

```
ctagcgaagg caccaggtac ttcttctttc gcgctgatca ccaccacccc catggtgccg      60
atcagcgaga aagatgaagt acctggtgcc ttct                                  94
```

<210> SEQ ID NO 17
<211> LENGTH: 415
<212> TYPE: PRT
<213> ORGANISM: Arabidopsis thaliana

<400> SEQUENCE: 17

```
Met Glu Gly Lys Ala Ile Ala Thr Ser Leu Gly Gly Asp Arg Val Leu
1               5                   10                  15

Ile Phe Pro Cys Ser Pro Arg Ser Ser Phe Val Phe Thr Ser Arg Leu
            20                  25                  30

Ser Ser Leu Pro Leu Lys Arg Ala Ser Ile Gly Gly Ala Val Ser Cys
        35                  40                  45

Ser Gly Val Asn Gly Leu Thr Arg Trp Asn Ser Ile Val Ser Thr Arg
    50                  55                  60

Arg Leu Val Pro Val Arg Ser Ile Asn Ser Glu Ser Asp Ser Asp Ser
65                  70                  75                  80

Asp Phe Pro His Glu Asn Gln Gln Gly Asn Pro Gly Leu Gly Lys Phe
                85                  90                  95

Lys Glu Tyr Gln Glu Trp Asp Ser Trp Thr Ala Lys Phe Ser Gly Gly
            100                 105                 110

Ala Asn Ile Pro Phe Leu Met Leu Gln Leu Pro Gln Ile Ile Leu Asn
        115                 120                 125

Thr Gln Asn Leu Leu Ala Gly Asn Asn Thr Ala Leu Ser Ala Val Pro
    130                 135                 140

Trp Leu Gly Met Leu Thr Gly Leu Leu Gly Asn Leu Ser Leu Leu Ser
145                 150                 155                 160

Tyr Phe Ala Lys Lys Arg Glu Lys Glu Ala Ala Val Val Gln Thr Leu
                165                 170                 175

Gly Val Val Ser Thr His Ile Val Leu Ala Gln Leu Thr Met Ala Glu
            180                 185                 190

Ala Met Pro Ile Gln Tyr Phe Val Ala Thr Ser Ala Val Val Thr Ile
        195                 200                 205

Gly Leu Ile Val Asn Cys Leu Tyr Tyr Phe Gly Lys Leu Ser Lys Thr
```

| | | | | | | | | | | | |
|---|---|---|---|---|---|---|---|---|---|---|---|
| | | 210 | | | | 215 | | | | 220 | |
| Val | Trp | Gln | Leu | Trp | Glu | Asp | Val | Ile | Thr | Ile | Gly Gly Leu Ser Val |
| 225 | | | | | 230 | | | | | 235 | 240 |

Val Trp Gln Leu Trp Glu Asp Val Ile Thr Ile Gly Gly Leu Ser Val
225                          230                          235                240

Leu Pro Gln Ile Met Trp Ser Thr Phe Val Pro Leu Val Pro Asn Ser
                     245                     250             255

Ile Leu Pro Gly Thr Thr Ala Phe Gly Ile Ala Val Ala Ala Ile Ile
            260                   265                  270

Met Ala Arg Thr Gly Lys Leu Ser Glu Lys Gly Val Arg Phe Val Gly
         275                   280                  285

Ser Leu Ser Gly Trp Thr Ala Thr Leu Met Phe Met Trp Met Pro Val
290                          295                          300

Ser Gln Met Trp Thr Asn Phe Leu Asn Pro Asp Asn Ile Lys Gly Leu
305                         310                     315              320

Ser Ser Ile Thr Met Leu Leu Ser Met Met Gly Asn Gly Leu Met Ile
            325                   330                  335

Pro Arg Ala Leu Phe Ile Arg Asp Leu Met Trp Leu Thr Gly Ser Leu
         340                   345                  350

Trp Ala Thr Leu Phe Tyr Gly Tyr Gly Asn Ile Leu Cys Leu Tyr Leu
     355                   360                  365

Val Asn Cys Thr Ser Gln Ser Phe Phe Val Ala Ala Thr Ile Gly Leu
370                          375                     380

Ile Ser Trp Ile Gly Leu Ala Leu Trp Arg Asp Ala Val Ala Tyr Gly
385                         390                     395              400

His Asn Ser Pro Phe Arg Ser Leu Lys Glu Leu Val Phe Gly Pro
         405                   410                  415

<210> SEQ ID NO 18
<211> LENGTH: 1248
<212> TYPE: DNA
<213> ORGANISM: Arabidopsis thaliana

<400> SEQUENCE: 18

| | |
|---|---|
| atggaaggta aagccatcgc gacgtctctc ggtggtgatc gtgtattgat attcccgtgt | 60 |
| tctcctcgct cttccttcgt ttttacatcc cggctctcta gcctgcctct aaagcgtgcg | 120 |
| tctatcggtg gtgctgtctc ttgttccggc gtcaatggct tgactcggtg gaattccatt | 180 |
| gtttcgactc gccgactcgt tcctgttcgt tcaattaact cggaatcgga ctcggactcc | 240 |
| gacttccctc acgagaatca gcagggaaat ccaggtttgg ggaaatttaa ggaataccaa | 300 |
| gaatgggact catggacggc caagttctcc ggtggagcaa acattccgtt tctcatgctc | 360 |
| caattgcctc agatcatcct caatacccag aatcttttgg cgggaaacaa taccgctctt | 420 |
| tcggctgtcc catggctggg aatgttgact ggtttgttag gaaacctttc gttgctttct | 480 |
| tattttgcta agaagagaga aaagaagca gctgtggtgc aaacactggg agtggtctct | 540 |
| actcacattg tgcttgcaca gctcacaatg gctgaagcaa tgcctattca gtattttgtt | 600 |
| gctacttcag ctgttgtcac catcggtctc attgtgaact gtttgtacta tttcggtaag | 660 |
| cttagcaaaa ctgtgtggca actgtgggaa gacgttatca ctattggtgg actctccgtt | 720 |
| cttcctcaaa tcatgtggtc aacatttgtc cctcttgtac aaacagtat cttgcctggg | 780 |
| acaactgctt ttggtattgc tgtggcagct ataatcatgg ctcgaactgg gaaactttca | 840 |
| gagaaaggtg ttaggtttgt agggtctta tctggatgga cagcaactct tatgttcatg | 900 |
| tggatgccag tttcccaaat gtggacaaat tttctaaacc cggacaacat aaaaggctta | 960 |
| tcgtcaatca caatgttgct ctcgatgatg ggaaacgggc ttatgatccc tcgagcacta | 1020 |

-continued

```
tttatccgtg atttgatgtg gctcactggt tcgctatggg caactctctt ttatggatat    1080
ggaaatattc tttgcttata cctggtaaat tgcaccagcc agtcattctt cgtggcagct    1140
acaattggtt tgatctcatg gataggactg gctttgtgga gagatgcagt ggcttatggt    1200
cacaactcgc cgtttagatc tttgaaagaa cttgtttttg gaccgtaa                 1248
```

<210> SEQ ID NO 19
<211> LENGTH: 371
<212> TYPE: PRT
<213> ORGANISM: Chlamydomonas reinhardtii

<400> SEQUENCE: 19

```
Met Leu Gln Pro Ala Pro Ala Arg Ser Phe Ser Gly Met Glu Gly Arg
1               5                   10                  15

Arg Thr Thr Gly Thr Arg Thr Leu Val Thr Val Ser Ser Arg Lys Lys
            20                  25                  30

Pro Val Pro Pro Leu His Ala Gly Ala Thr Ser Gly Pro Ala Ser Asp
        35                  40                  45

Ser Gln Arg Trp Asn Ala Leu Thr Asp Lys Leu Val Ala Ala Ser Ser
    50                  55                  60

Ile Pro Phe Ser Ile Leu Val Leu Pro Gln Val Val Gln Asn Ala Ile
65                  70                  75                  80

Asn Met Ala Gly Gly His Pro Thr Ala Leu Ser Ile Ile Ser Trp Glu
                85                  90                  95

Gly Tyr Leu Ser Ala Met Phe Gly Asn Thr Leu Met Cys Ser His Phe
            100                 105                 110

Ala Ala Ser Gly Glu Arg Ser Ala Val Asn Val Gln Leu Val Gly Ile
        115                 120                 125

Leu Asn Asn Phe Leu Ile Leu Thr Gln Val Ala Leu Ala Gly Phe Met
    130                 135                 140

Pro Leu Ala Val Phe Leu Ala Ala Ala Phe Thr Ala Phe Ala Thr
145                 150                 155                 160

Phe Met Asn Leu Ala Arg Val Ala Ala Leu Gly Ala Ala Gln Pro
                165                 170                 175

Ala Asp Glu Lys Trp Gly Ser Trp Gln Met Trp Gln Leu Gly Ser Gly
            180                 185                 190

Leu Val Gly Leu Ala Val Val Pro Gln Val Leu Tyr Asn Thr Val Ser
        195                 200                 205

Pro Ala Ala Ser Thr Leu Leu Pro Phe Ile Cys Thr Leu Gly Leu Leu
    210                 215                 220

Gly Ala Val Leu Gly Leu Arg Leu Ser Ser Lys Gly Gly Ser Asp Ala
225                 230                 235                 240

Ala Thr Leu Val Arg Gln Leu Pro Gly Trp Gly Ala Thr Leu Leu Phe
                245                 250                 255

Ala Leu Ser Pro Leu Pro Gln Leu Val Arg Asn Leu Leu Glu Pro Gln
            260                 265                 270

Ser Leu Glu Gly Leu Ser Val Gly Thr Met Leu Leu Ala Leu Leu Gly
        275                 280                 285

Asn Ala Leu Met Val Pro Arg Ala Leu Phe Val Arg Asp Val Val Trp
    290                 295                 300

Leu Ser Gly Thr Cys Trp Ala Cys Val Ala Gly Trp Gly Gln Leu Phe
305                 310                 315                 320

Ser Met Phe Arg Ser Ala Ser Ala Ala Thr Gly Arg Arg Phe Leu Asp
                325                 330                 335
```

```
Pro Trp Leu Phe Phe Ser Ile Thr Gly Ala Leu Leu Tyr Thr Gly
            340                 345                 350

Tyr Val Val Val Gln His Arg Arg Ala Thr Ala Ala Ala Ser Pro
            355                 360                 365

Arg Pro Ala
    370

<210> SEQ ID NO 20
<211> LENGTH: 1116
<212> TYPE: DNA
<213> ORGANISM: Chlamydomonas reinhardtii

<400> SEQUENCE: 20
atgttgcaac cggcaccggc aaggagtttt tcggggatgg aagggcgacg gacaacaggc      60
acgcgaacgc tggtgactgt cagtagccgg aaaaagcccg tgcccccgtt gcatgcggga     120
gcaacgagcg gtccggcaag cgacagccag cgatggaatg cgctcacgga caagctggtg     180
gctgcatcca gcattccgtt ctctattttg gtgcttccgc aagtcgtcca gaatgccatc     240
aacatggctg gcggccaccc cacggccctg tccattatca gctgggaggg ctacctctct     300
gccatgttcg gcaacacatt aatgtgcagc catttcgcgg cgtcaggcga gcgcagcgcc     360
gtaaacgtgc agcttgtggg aatcctcaac aacttcctca ttctcacaca ggtggctctt     420
gccggcttca tgccgctcgc ggtgttttg gcggcggcgg ccttcacggc ctttgccact      480
tttatgaacc tggcacgcgt ggcggcgctg gcgggcgcag cgcagccggc ggacgagaag     540
tggggcagct ggcagatgtg gcagctgggc agcgggctgg tggggctggc ggtggtgccg     600
caggtgctct acaacaccgt gtccccggcg gcatccacgc tgctgcccct catttgcacg     660
cttgggctgc ttggagcggt gctagggcta cggctgtcgt ccaagggcgg tagcgacgcg     720
gcaacgctgg tgcggcagct gccgggctgg ggcgccacgc tgctgtttgc gctgtcgccg     780
ctaccgcagc tggtccgcaa cctgcttgag ccacagagcc tggagggcct gagcgtgggc     840
accatgctgc tggcgctgct gggcaacgcg ctcatggtgc cgcgggcgct gttcgtgcgc     900
gacgtggtgt ggctcagcgg cacctgctgg gcctgcgtag cgggctgggg tcagctgttc     960
agcatgttcc gcagcgcgtc ggcggccaca gggcggcgct tcctggaccc ctggctgttc    1020
ttctccatca ccgggcgct gctgctgtac actggctacg tggtggtgca gcaccggaga    1080
gccacagcgg cggcagcaag cccgcggccc gcataa                             1116
```